US011351282B2

(12) United States Patent
Lim et al.

(10) Patent No.: US 11,351,282 B2
(45) Date of Patent: Jun. 7, 2022

(54) STERILIZER AND STERILIZATION METHOD THEREOF

(71) Applicant: PLASMAPP CO., LTD., Daejeon (KR)

(72) Inventors: Youbong Lim, Daejeon (KR); Seunghun Lee, Seoul (KR)

(73) Assignee: PLASMAPP CO., LTD., Daejeon (KR)

( * ) Notice: Subject to any disclaimer, the term of this patent is extended or adjusted under 35 U.S.C. 154(b) by 273 days.

(21) Appl. No.: 16/614,154

(22) PCT Filed: Feb. 13, 2019

(86) PCT No.: PCT/KR2019/001785
§ 371 (c)(1),
(2) Date: Nov. 15, 2019

(87) PCT Pub. No.: WO2019/160339
PCT Pub. Date: Aug. 22, 2019

(65) Prior Publication Data
US 2020/0069826 A1    Mar. 5, 2020

(30) Foreign Application Priority Data

Feb. 13, 2018  (KR) .................. 10-2018-0018053
Oct. 29, 2018  (KR) .................. 10-2018-0129526

(51) Int. Cl.
*A61L 2/20*      (2006.01)
*A61L 2/24*      (2006.01)
(Continued)

(52) U.S. Cl.
CPC ............ *A61L 2/20* (2013.01); *A61L 2/24* (2013.01); *A61L 2/26* (2013.01); *B65B 55/027* (2013.01);
(Continued)

(58) Field of Classification Search
CPC ..... A61L 2/20; A61L 2/24; A61L 2/26; A61L 2202/11; A61L 2202/14; A61L 2202/15; A61L 2202/24; B65B 55/027
See application file for complete search history.

(56) References Cited

FOREIGN PATENT DOCUMENTS

EP         1 110 559 A2    6/2001
KR    10-2018-0006867 A    1/2018

OTHER PUBLICATIONS

Englsih Language Machine Translation KR1020180006867; Jan. 2018 (Year: 2018).*

(Continued)

*Primary Examiner* — Sean E Conley
(74) *Attorney, Agent, or Firm* — Sughrue Mion, PLLC

(57) ABSTRACT

The present invention relates to a sterilizer using an impermeable sealed container and a sterilization method thereof, and more particularly, to a sterilizer using an impermeable sealed container and a sterilization method thereof, the sterilizer being capable of diagnosing residual moisture to improve sterilization reliability and increase sterilization efficiency, and directly being connected to a vaporizer. More specifically, the present invention relates to a technique for solving the problems of taking a long time to sterilize and inefficiency in removing and purifying a sterilant that remains after the sterilization is completed, and for improving the problems of difficulty in ensuring sterilization reliability and inefficiency in using a sterilizer due to the same drying process irrespective of actual residual moisture.

19 Claims, 25 Drawing Sheets

(51) Int. Cl.
*A61L 2/26* (2006.01)
*B65B 55/02* (2006.01)
(52) U.S. Cl.
CPC ........ *A61L 2202/11* (2013.01); *A61L 2202/14* (2013.01); *A61L 2202/15* (2013.01); *A61L 2202/24* (2013.01)

(56) References Cited

OTHER PUBLICATIONS

Communication dated Jun. 15, 2021, from the Korean Intellectual Property Office in application No. 10-2019-7038277.
International Search Report dated Jun. 11, 2019 issued by the International Searching Authority in International Application PCT/KR2019/001785.
Communication issued in the European Patent Office in corresponding European Patent Application No. 19753834.1 dated Oct. 12, 2021.

\* cited by examiner

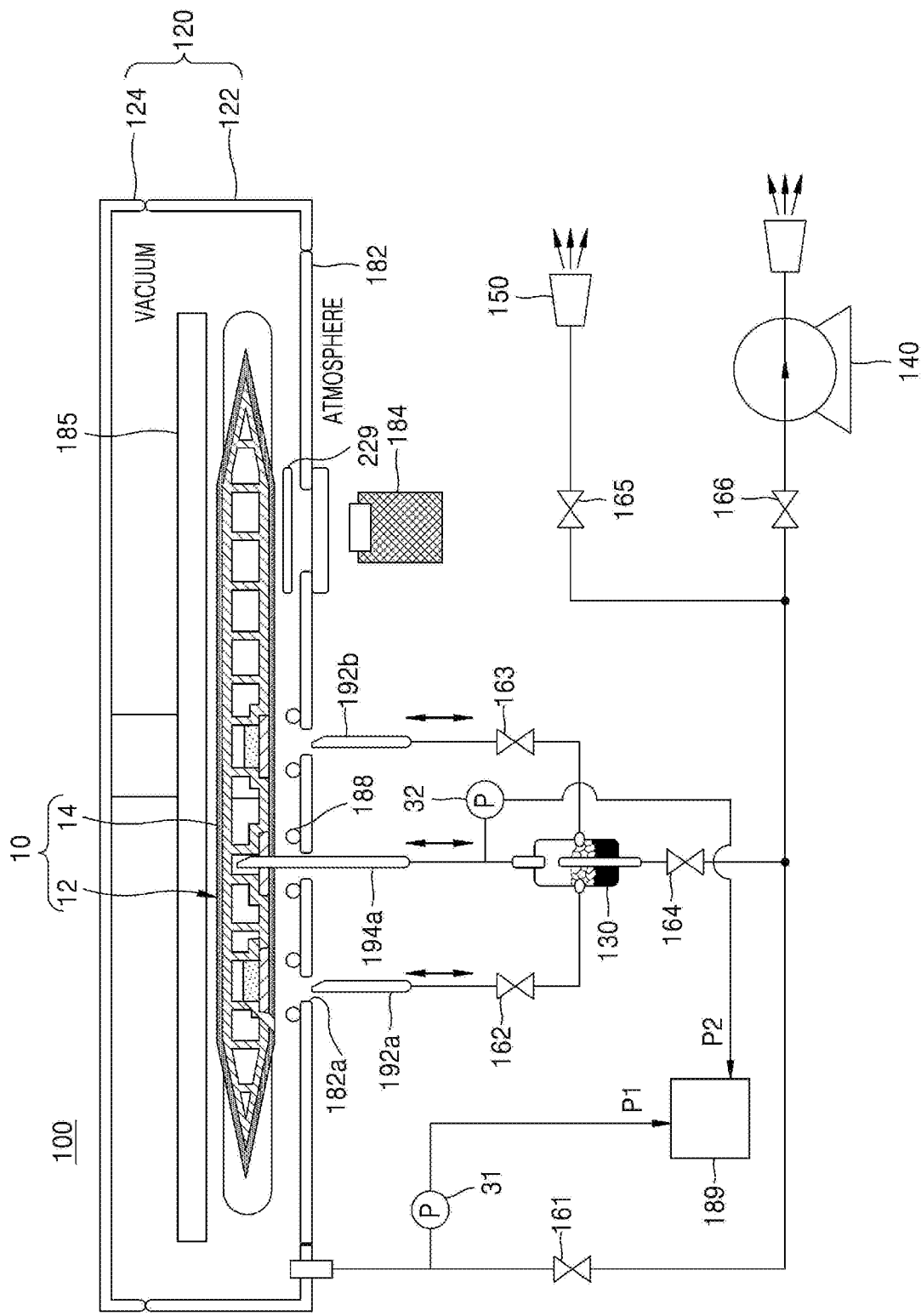

STERILIZER AND STERILIZATION METHOD THEREOF

TECHNICAL FIELD

The present invention relates to a sterilizer using an impermeable sealed container and a sterilization method thereof, and more particularly, to a sterilizer using an impermeable sealed container and a sterilization method thereof, the sterilizer being capable of diagnosing residual moisture to improve sterilization reliability and increase sterilization efficiency, and directly being connected to a vaporizer.

BACKGROUND ART

Various sterilizers have been developed for disinfection and sterilization of various medical devices and treatment/procedure tools. However, a conventional general medical sterilizer has a chamber having a large volume of several tens of liters or more, and a sterilant is indirectly injected through a film having selective permeability in a state in which a sterilized article is packaged in the chamber. Thus, the sterilant supplied to the chamber has a problem that the efficiency of being delivered to the sterilized article is greatly reduced, and it takes a long time for the sterilant to be sufficiently delivered to the sterilized article. In addition, since the sterilant remaining after the sterilization is completed needs to be discharged through a packaging pouch, there is a problem that it takes a long time in the process of purification because of the low efficiency.

Also, a chemical sterilizer used in the medical industry performs a sterilization process using a sterilant such as hydrogen peroxide. A sterilant performs the sterilization process by deactivating microorganisms remaining in a target object through an oxidation process.

The sterilization is difficult to ensure process reliability due to impurities remaining on a surface of the target object. In particular, residual moisture may cause loss and dilution of the sterilant, which may prevent oxidation of the microorganisms to an intended level. Therefore, the sterilization process is difficult to guarantee sterilization reliability. In order to solve such a problem, a sufficient (e.g., 1 hour) drying process may be added before the sterilization process. However, a long drying process increases the overall sterilization process time, lowering the product efficiency, and increasing the maintenance burden of a vacuum device such as a vacuum pump in a process of removing excess moisture. In addition, a dry state of the target object varies from case to case, so the sterilization reliability cannot be guaranteed.

DETAILED DESCRIPTION OF THE INVENTION

Technical Problem

As described above, since a conventional general medical sterilizer does not sufficiently deliver a sterilant to a sterilized article, also takes a long time to sterilize, and is less efficient in removing and purifying the sterilant that remains after the sterilization is completed, the present invention seeks to improve this.

The present invention is directed to a sterilization preparation process that solves the problems of a conventional chemical sterilizer treatment process, which is difficult to guarantee sterilization reliability due to the same drying process irrespective of actual residual moisture and decreases the efficiency of sterilizer use.

The present invention is directed to a sterilization preparation process that solves frequent maintenance problems caused by excessive moisture exposure of vacuum devices used in conventional chemical sterilizers.

The present invention is directed to providing of sterilization reliability by measuring the amount of moisture remaining in a target object before a sterilization process and by adding a drying process based on the measured amount of residual moisture. It is possible to maximize the efficiency of sterilizer use by reducing time of the entire sterilization process by performing a drying process of the minimum time according to the amount of residual moisture.

The present invention is not limited to the above objectives, but other objectives not described herein may be clearly understood by those of ordinary skill in the art from descriptions below.

Technical Solution

The means for solving the problems to be solved according to the present invention are as follows.

According to an aspect of the present invention, a sterilizer includes an impermeable sealed container directly connected to a vaporizer.

Preferably, the impermeable sealed container is flexible and elastic, thereby freeing contraction and expansion of the volume according to external pressure.

Also preferably, the vaporizer is connected to a vacuum pump and an exhaust port to perform independent pressure control through a valve.

More preferably, the vacuum pump and the exhaust port are also connected to a chamber to enable independent pressure control through the valve.

Alternatively preferably, the vaporizer is directly connected to the impermeable sealed container to control pressure of the container by controlling pressure of the vaporizer.

Alternatively more preferably, the vacuum pump and the exhaust port are also connected to a plasma source or a catalyst for purifying a sterilant.

Alternatively preferably, the impermeable sealed container is supplied with air and a sterilant through the vaporizer.

Even more preferably, the supply of air is made through the vaporizer to increase heating efficiency inside the impermeable sealed container.

Still more preferably, the effective volume of a sterilized article is checked by measuring the time that the air is supplied to the impermeable sealed container.

Accuracy of the effective volume check is increased by measuring the time at which internal pressure of the impermeable sealed container reaches a specific value.

In addition, in order to increase the accuracy of the volume check, the air is repeatedly injected with an air injection time and a holding time.

Preferably, the holding time allows the impermeable sealed container to expand sufficiently to increase the accuracy of the volume check.

Also preferably, time resolution is controlled by adjusting a ratio of the injection time and the holding time.

Alternatively preferably, introduced is a method of measuring the number of venting cycles until the internal pressure of the impermeable sealed container reaches a specific value, as non-integer rational numbers, using a median formula.

Meanwhile, when the effective volume check of the sterilized article is completed, the air supply is cut off and a change in pressure per unit time in the impermeable sealed container is measured to detect a pouch sealing error of the impermeable sealed container.

Meanwhile, an optimized heating process is provided by measuring the effective volume of the sterilized article and varying the heating time according to the value.

According to another aspect of the present invention, a sterilization method includes (S1) initializing to identify a chamber, an impermeable sealed container containing a sterilized article, and a locking device; (S2) heating and drying the chamber and the impermeable sealed container; (S3) sterilizing; and (S4) residue checking, purifying, and completing the process.

(S2) The heating and drying of the chamber and the impermeable sealed container includes (P1) initial pumping to prepare a low level vacuum; (P2) checking an effective volume of the sterilized article; (P3) heating the impermeable sealed container and the chamber; (P4) checking residual moisture; and (P5) drying and vacuuming to obtain base pressure.

In (P1) the initial pumping of preparing the low level vacuum, pressure of the chamber is relatively low compared to pressure of the impermeable sealed container, and thus a sufficient channel may be formed in a flexible sealed container such as a pouch even during the pumping process to form a vacuum.

In (P2) the checking of the effective volume of the sterilized article, the effective volume is checked by measuring an internal pressure value of the impermeable sealed container and measuring time to reach a specific value.

In more detail, after (P1) the initial pumping, the channel between the vaporizer and the chamber is opened to match the pressure value, and air is injected into the impermeable sealed container, but an injection time of the air and the time for blocking the injection and holding the blocking are separated and repeated to increase the accuracy of checking the effective volume.

Time resolution is controlled by adjusting a ratio of the injection time to the holding time.

In addition, the accuracy of the effective volume check is increased by measuring the number of venting cycles until reaching a specific value, as non-integer rational numbers, using a median formula.

After (P2) the checking of the effective volume of the sterilized article, in order to confirm the lamination error or damage of the impermeable sealed container, a channel is blocked and the internal pressure of the impermeable sealed container is measured. After measuring a change in the internal pressure of the impermeable sealed container in time to detect the lamination error or damage, (P3) heating of the impermeable sealed container and the chamber is performed.

In (P3) the heating the impermeable sealed container and the chamber, the inside of the chamber is at pressure lower than atmospheric pressure, and thus air may be introduced into the sealed container without a separate device.

In particular, the temperature of air introduced from the outside is controlled through temperature control of a supply pipe.

In addition, forced convection occurs inside the sealed container by using the introduced air to increase heating efficiency of the sterilized article.

A time required for the heating varies depending on the effective volume of the sterilized article.

In (P4) the checking of residual moisture, when the inside of the sealed container reaches pressure lower than water vapor pressure through vacuum exhaust, the amount of water evaporated is measured to estimate the total amount of water.

In addition, when the inside of the sealed container reaches certain pressure through the vacuum exhaust, the valve is closed to isolate the inside of the impermeable sealed container, and then the change in pressure is measured.

Also, a rate of the change in pressure per unit time increases in proportion to the amount of moisture in the impermeable sealed container.

According to the measured rate of the change in pressure per unit time, in (P5) the drying and vacuuming to obtain base pressure, the drying process time is variable.

According to another aspect of the present invention, a residual water diagnostic method includes: initially evacuating a sterilization container containing a target object to a vacuum for a first time interval; stopping the initial evacuation of the sterilization container and calculating a first rate of pressure rise in time of the sterilization container for a second time interval; performing secondary exhaust of the sterilization container for a third time interval when the first rate of pressure rise is within a set range; and stopping the secondary exhaust of the sterilization container and calculating a second rate of pressure rise in time of the sterilization container for a fourth time interval.

According to an embodiment of the present invention, pressure of the sterilization container after the initial evacuation may be at or below pressure corresponding to a boiling point at the temperature of the sterilization container.

According to an embodiment of the present invention, the temperature of the sterilization container is room temperature and the pressure of the sterilization container after the initial evacuation may be 30 Torr or less.

According to an embodiment of the present invention, a set range of the first rate of pressure rise may be 0 Torr/sec to 0.2 Torr/sec.

According to an embodiment of the present invention, the first time interval may be 20 seconds to 90 seconds, the second time interval may be 10 seconds to 30 seconds, the third time interval may be 10 seconds to 50 seconds, and the fourth time interval may be 10 seconds to 40 seconds.

According to an embodiment of the present invention, the method may further include additionally drying and evacuating the sterilization container to dry the target object when the second rate of pressure rise is within a set range.

According to an embodiment of the present invention, the set range of the second rate of pressure rise may be 0 Torr/sec to 0.4 Torr/sec.

According to an embodiment of the present invention, the sterilization container may be a vacuum pouch in a vacuum chamber.

According to an embodiment of the present invention, the sterilization container may be a vacuum chamber occupying a fixed space.

According to another aspect of the present invention, a sterilization method includes: initially evacuating a sterilization container containing a target object to a vacuum for a first time interval and stopping the initial evacuation of the sterilization container to calculate a first rate of pressure rise in time of the sterilization container for a second time interval; and sterilizing the sterilization container by injecting a sterilant into the sterilization container.

According to an embodiment of the present invention, the sterilization method may further include: venting the sterilization container to the atmosphere when the first rate of pressure rise is greater than or equal to a first threshold.

According to an embodiment of the present invention, the sterilization method may further include: performing additional evacuation when the first rate of pressure rise is less than or equal to a second threshold.

According to an embodiment of the present invention, the sterilization method may further include: evacuating the sterilization container to a vacuum for a third time interval after calculating the first rate of pressure rise, and stopping the evacuation of the sterilization container and calculating a second rate of pressure rise in time of the sterilization container for a fourth time interval.

According to an embodiment of the present invention, the calculating of the second rate of pressure rise may be performed when the first rate of pressure rise is within a set range.

According to an embodiment of the present invention, the sterilization method may further include: venting the sterilization container to the atmosphere when the second rate of pressure rise is greater than or equal to a third threshold.

According to an embodiment of the present invention, the sterilization method may further include: performing additional evacuation when the second rate of pressure rise is less than or equal to a fourth threshold.

According to an embodiment of the present invention, the sterilization method may further include: evacuating and drying and the sterilization container to dry the target object when the second rate of pressure rise is within a set range.

According to an embodiment of the present invention, an evacuation time for performing evacuating and drying may be proportional to the second rate of pressure rise.

According to an embodiment of the present invention, the sterilization method may further include: venting the sterilization container when pressure of the sterilization container after the evacuating and drying is at or below reference pressure.

According to an embodiment of the present invention, the set reference value after the drying and evacuating may be 1 Torr.

According to an embodiment of the present invention, the sterilization container is a vacuum pouch and may be in a vacuum chamber.

According to another aspect of the present invention, a residual water diagnostic method includes: evacuating a sterilization container at least once to form a vacuum, and then measuring a rate of pressure rise due to vaporization of residual moisture remaining in the sterilization container while the evacuation is interrupted and predicting the amount of residual moisture remaining in a target object.

According to an embodiment of the present invention, the amount of residual moisture may be predicted by repeating the evacuation of the sterilization container and the interruption of the evacuation twice.

According to another aspect of the present invention, a sterilization device includes: a sterilization pouch containing a target object therein and being sealed to maintain the target object in a vacuum state; a vacuum chamber having a door and containing the sterilization pouch; a needle extracting a sterilant stored in the sterilization pouch, injecting the extracted sterilant into the sterilization pouch, and evacuating the sterilization pouch in a vacuum state; a vacuum pump evacuating the sterilization pouch and the vacuum chamber; and a pressure gauge measuring pressure of the sterilization pouch.

According to an embodiment of the present invention, the sterilization device may further include a processor predicting the amount of residual moisture in the sterilization pouch by using an output signal of the pressure gauge with the evacuation of the sterilization pouch stopped.

According to another aspect of the present invention, a sterilization device includes: a vacuum chamber containing a target object therein and being sealed to maintain the target object in a vacuum state; a sterilant cassette disposed in the vacuum chamber to store a sterilant and to inject the sterilant into the vacuum chamber; a vacuum pump evacuating the vacuum chamber; a needle extracting a sterilant stored in the sterilant cassette and injecting the extracted sterilant into the vacuum chamber; a pressure gauge measuring pressure of the vacuum chamber; and a controller predicting the amount of residual moisture in the vacuum chamber by using an output signal of the pressure gauge with the evacuation of the vacuum chamber stopped.

According to another aspect of the present invention, a sterilization device includes: a vacuum chamber containing a target object therein and being sealed to maintain the target object in a vacuum state; a vaporizer injecting a sterilant into the vacuum chamber; a vacuum pump evacuating the vacuum chamber; a pressure gauge measuring pressure of the sterilization pouch; and a controller predicting the amount of residual moisture in the sterilization pouch by using an output signal of the pressure gauge with the evacuation of the vacuum chamber stopped.

Advantageous Effects of the Invention

Effects obtained by the present invention through the means for solving the above problems are as follows.

According to direct connection between a vaporizer and an impermeable sealed container, the effective volume of a sterilized article may be checked by measuring the amount of air supplied to the impermeable sealed container and the time the air is supplied.

In addition, by measuring the time when pressure inside the impermeable sealed container reaches a certain value, the accuracy of the effective volume check of the sterilized article may increase and the ratio of an injection time and a holding time of air and a sterilant may be adjusted, thereby specifically controlling a time required for sterilization of the sterilized article by characteristics. In addition, a heating time for the impermeable sealed container may vary according to the effective volume of the sterilized article, and thus temperature rise may be efficiently controlled.

Meanwhile, the amount of internal moisture may be estimated by measuring a rate of a change in pressure inside the impermeable sealed container, and a drying process time may be controlled during sterilization according to the amount of the internal moisture. Also, an hourly change in the pressure inside the impermeable sealed container may be measured to detect sealing errors and tears in the impermeable sealed container.

Meanwhile, the present invention predicts the amount of residual moisture by measuring pressure at which a vacuum is formed and a rate of pressure rise (ROR) using a vacuum gauge connected to a sterilization chamber and/or a vacuum pouch. A drying process based on the predicted amount of residual moisture is performed to ensure sterilization reliability and maximize the efficiency of sterilizer use.

Meanwhile, the present invention may measure initial vacuum forming pressure and the ROR and stop the process when there is excessive moisture to prevent excessive moisture exposure of a vacuum device and solve a maintenance problem.

Meanwhile, sterilizers according to the present invention are expected to be used in a variety of industries that use

BRIEF DESCRIPTION OF THE DRAWINGS

FIGS. 7A to 7E are conceptual views of a sterilization device according to an embodiment of the present invention.

BEST MODE OF THE INVENTION

Figure 1:
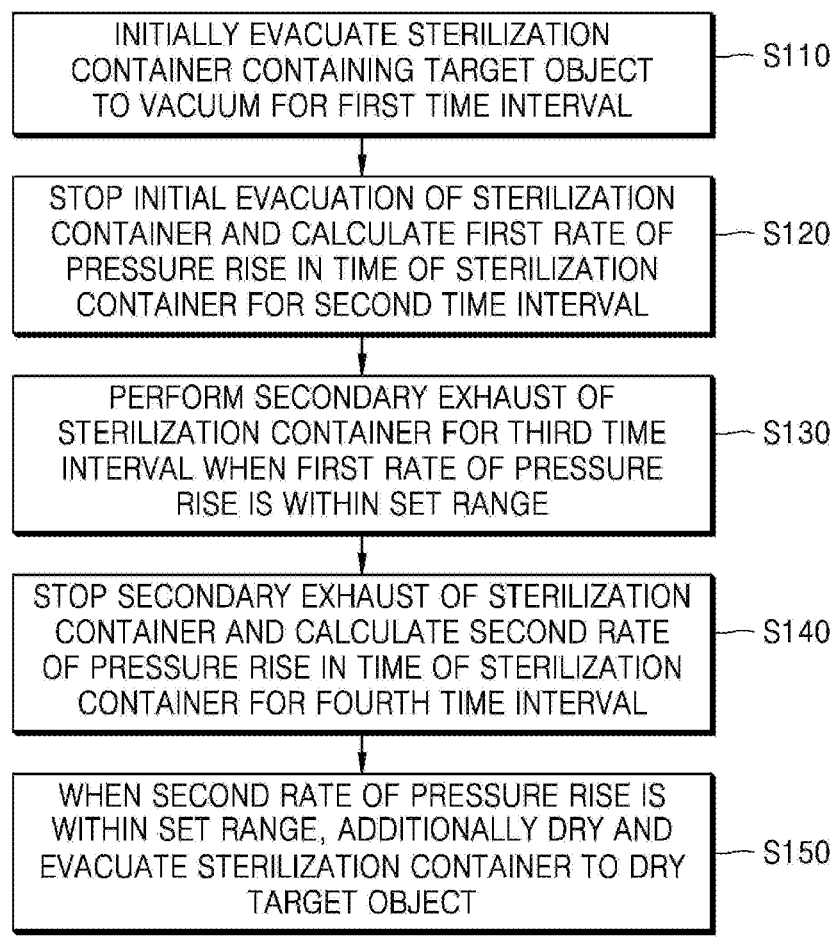
FIG. 1 is a flowchart illustrating a residual water diagnostic method according to an embodiment of the present invention.

The present invention is directed to a sterilizer including an impermeable sealed container directly connected to a vaporizer, and more particularly, to a sterilizer capable of supplying a sterilant directly to a sterilized article as the vaporizer is directly connected to the impermeable sealed container containing the sterilized article, but being vacuumed by itself.

The impermeable sealed container is used synonymously with the "pouch" used in the conventional sterilizer technique, and is referred to as an "impermeable sealed container" rather than a pouch to indicate "impermeable" which is one of the features of the present invention.

According to the above object, the present invention will be described in more detail.

At atmospheric pressure, water reaches a boiling point at 100° C. and may evaporate quickly. However, when a vacuum of about 30 Torr is formed even at room temperature, the moisture reaches a boiling point. After a vacuum at constant pressure is initially formed in this way, a change in pressure due to residual moisture vaporized and discharged from a target object may be measured to predict the amount of the residual moisture.

In a sterilization container having a volume V, if the pressure of air is P air and the pressure of water is P vapor, the total pressure P may be referred to as follows by a partial pressure law of gas.

$$P = P\text{air} - P\text{vapor}$$

A change amount ΔP of the total pressure P is equal to the sum of change amounts of respective partial pressures. The change amounts of the respective partial pressures may be expressed by the following equation according to the state equation of gas.

$$\Delta P = \Delta P air + \Delta P vapor = kT\left(\frac{\Delta N air}{V} + \frac{\Delta N vapor}{V}\right)$$

$$\Delta P = \Delta kT\left(\rho air \frac{\Delta mair}{Mair} + \rho vapor \frac{\Delta mvapoer}{Mvapor}\right)$$

Where ρ and M denote the density and molecular weight of each material. N air and N vapor are the number of air particles and the number of water vapor particles, respectively.

The derivative in time of pressure may be expressed as:

$$\frac{dP}{dt} = kT\left(\frac{\rho air}{Mair}\frac{dmair}{dt} + \frac{\rho vapor}{Mvapor}\frac{dmvapor}{dt}\right).$$

Where $dm_{air}/dt$ is a mass flow rate of air (including water) exiting by a vacuum pump and $dm_{vapor}/dt$ is a mass flow rate where moisture is converted into water vapor.

In this case, when a valve of a pipe connected to the vacuum pump is closed to isolate the sterilization container, the pressure is increased by the moisture coming out of the target object. This change in pressure in time is proportional to the amount of water evaporated per unit time. The amount of water evaporated per unit time is proportional to a surface area ($S_{vapor}$) with water distribution. This relationship may be expressed as:

$$\frac{dP}{dt} = kT\frac{\rho vapor}{Mvapor}\frac{dmvapor}{dt} \propto Svapor$$

The surface area of moisture depends on the shape in which the moisture is distributed. The surface area of moisture may be assumed as a as a relationship of a monotonically increasing function to the amount of moisture. Thus, the change in pressure in time may depend on the amount of residual moisture. In addition, according to an experimental result of the present invention, a rate of pressure rise in time of the sterilization container is proportional to the amount of water injected into the sterilization container.

In more detail, when the sterilization container is evacuated to a vacuum for a certain time, the pressure reached by the vacuum pump is measured. Next, the valve between the vacuum pump and the sterilization container is closed to stop the evacuation, and then a rate of pressure rise due to evaporation of moisture in the sterilization container is measured. The ROR predicts the amount of residual moisture. Subsequently, an optimized drying process is performed to remove the predicted residual moisture. The drying process may be accomplished by additional evacuation.

The present invention predicts the amount of residual moisture by measuring pressure at which a vacuum is formed and the ROR using a vacuum gauge connected to a sterilization chamber or a vacuum pouch (or a vacuum pouch) in a vacuum chamber. A drying process is provided to remove the predicted amount of residual moisture, ensuring sterilization reliability and maximizing the efficiency of sterilizer use.

The present invention may measure initial vacuum forming pressure and the ROR and stop the sterilization process in progress when there is excessive moisture to prevent excessive moisture exposure of a vacuum device and solve a maintenance problem.

A water diagnosis process according to an embodiment of the present invention measures the pressure reached through initial pumping and closes a valve connected to a vacuum pump to measure the ROR in an isolated state so as to determine whether there is excessive moisture inside a target object or the vacuum chamber.

A sterilization preparation process according to an embodiment of the present invention measures the initial pumping and the ROR, and again measures the pressure and ROR reached through vacuum formation through secondary exhaust, allowing accurate prediction of the residual moisture.

The sterilization preparation process according to an embodiment of the present invention may be performed by measuring vacuum reached pressure and the ROR using a pressure gauge connected to the sterilization chamber or the vacuum chamber.

FIG. 1 is a flowchart illustrating a residual water diagnostic method according to an embodiment of the present invention.

Figure 2:
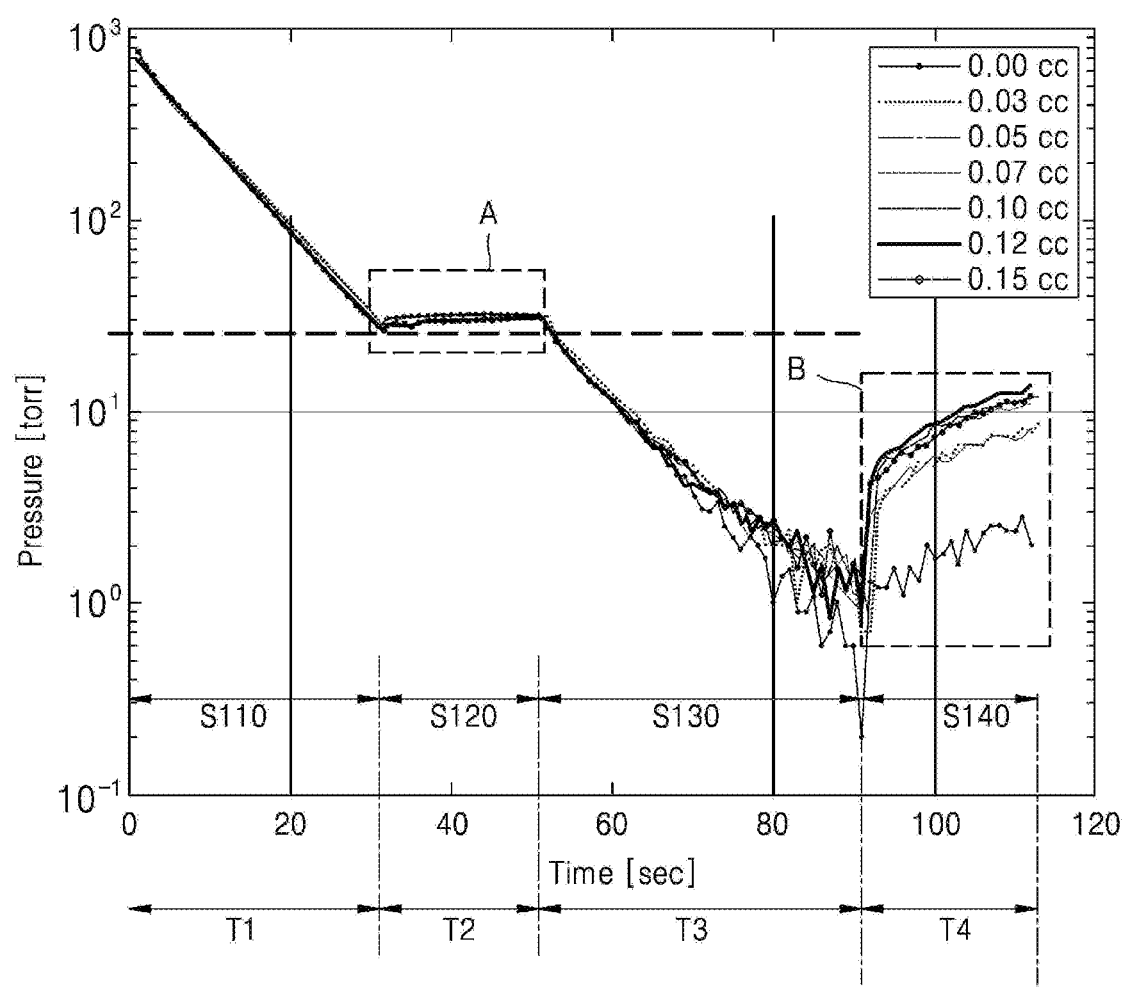
FIG. 2 is a view of an experimental result of measuring the pressure in time while varying the amount of water injected into a sterilization container.

FIG. 2 is a view of an experimental result of measuring the pressure in time while varying the amount of water injected into a sterilization container.

Figure 3:
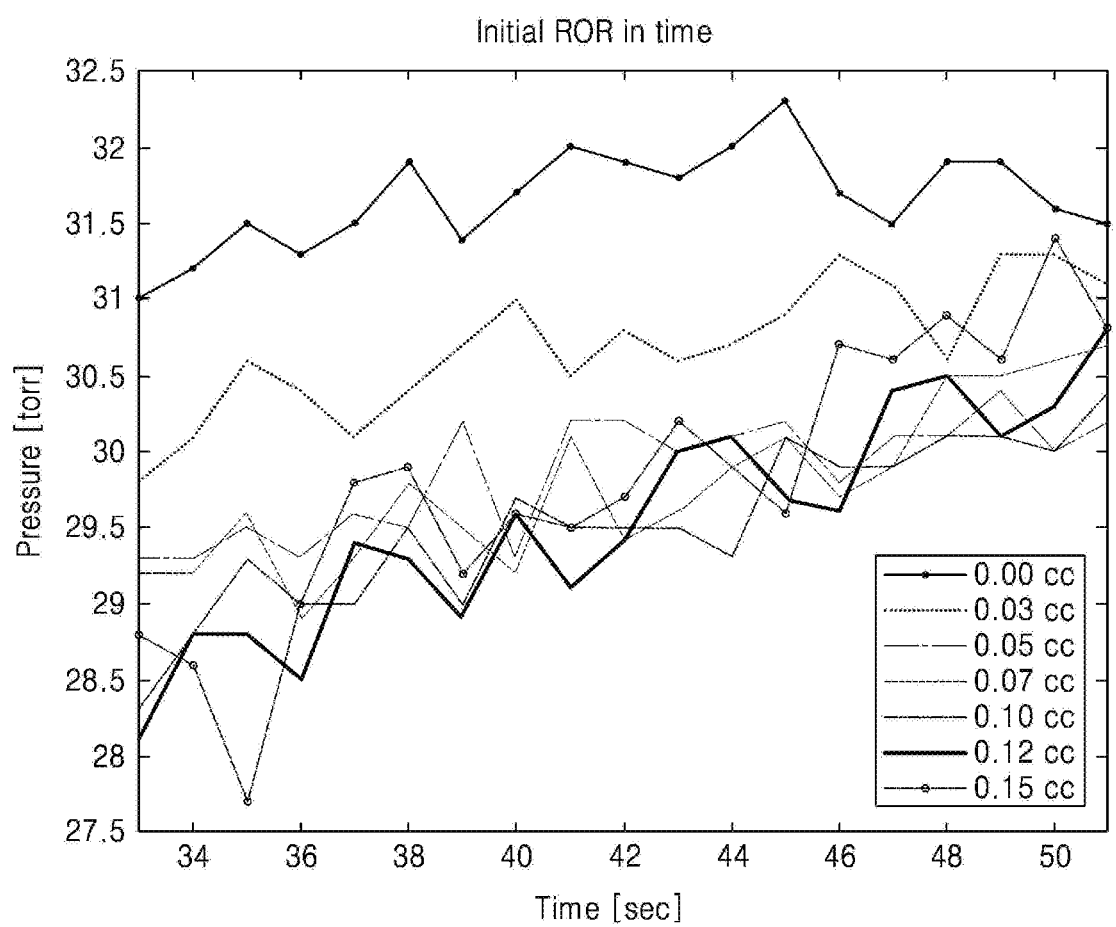
FIG. 3 is an enlarged view illustrating a change in pressure in a second time interval of FIG. 2.

FIG. 3 is an enlarged view illustrating a change in pressure in a second time interval of FIG. 2.

Figure 4:
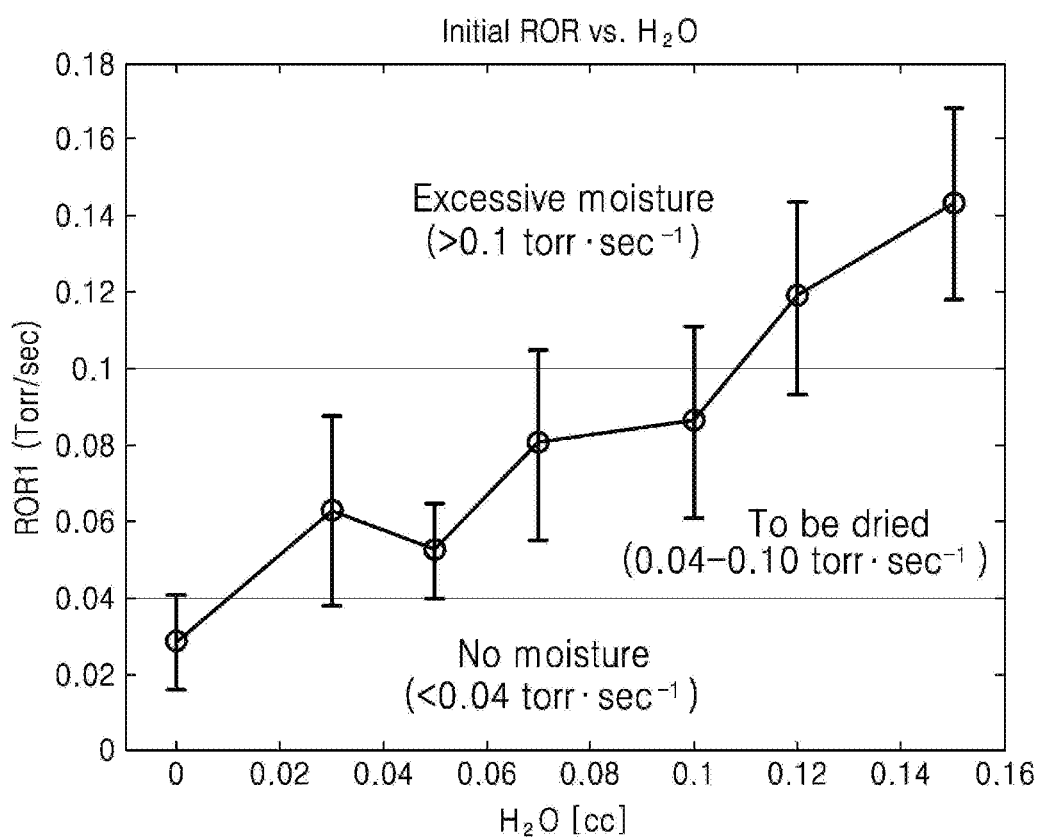
FIG. 4 is a view of an experimental result of displaying a first rate of a change in pressure of FIG. 3 according to the amount of water injected into a sterilization container.

FIG. 4 is a view of an experimental result of displaying a first rate of a change in pressure of FIG. 3 according to the amount of water injected into a sterilization container.

Figure 5:
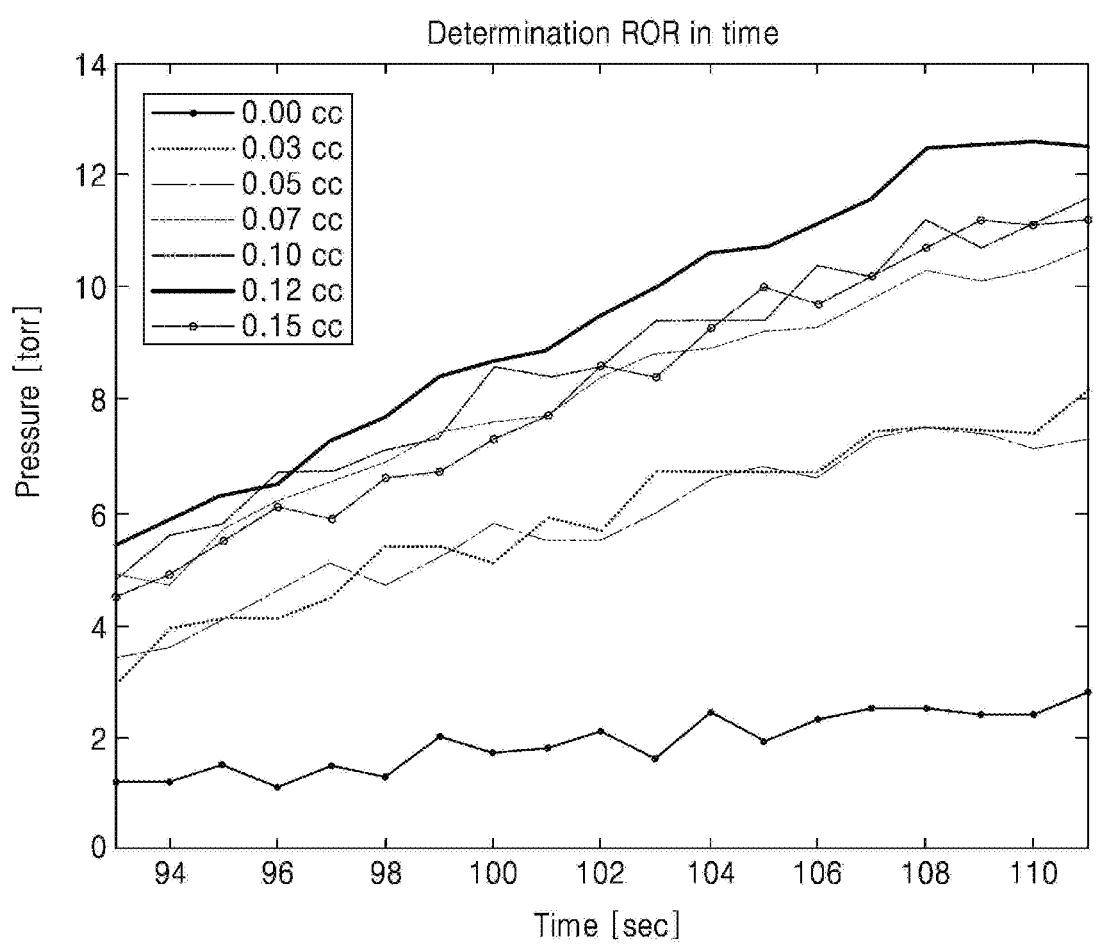
FIG. 5 is an enlarged view illustrating a change in pressure in a fourth time interval of FIG. 2.

FIG. 5 is an enlarged view illustrating a change in pressure in a fourth time interval of FIG. 2.

Figure 6:
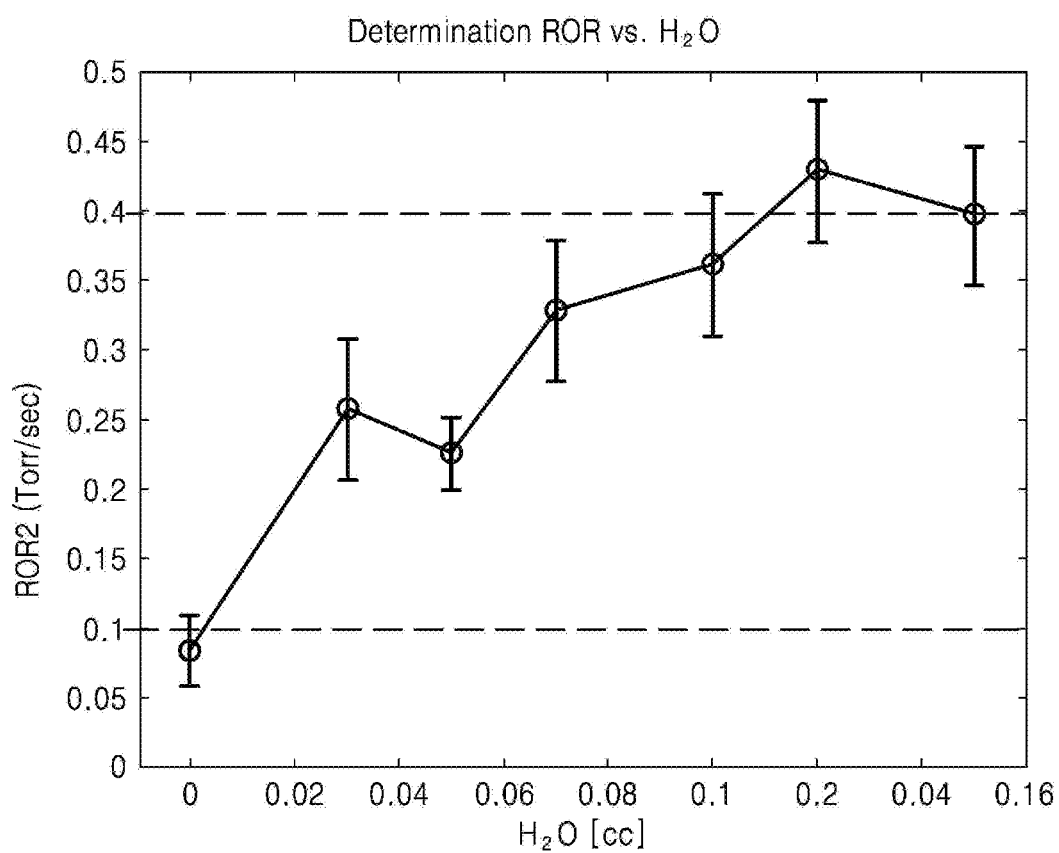
FIG. 6 is a view of an experimental result of displaying a second rate of a change in pressure of FIG. 5 according to the amount of water injected into a sterilization container.
Figure 7B:
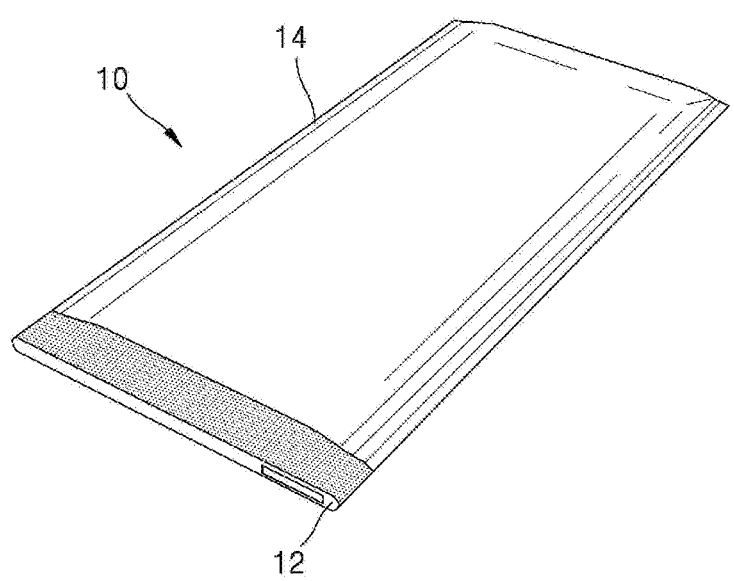
Figure 7C:
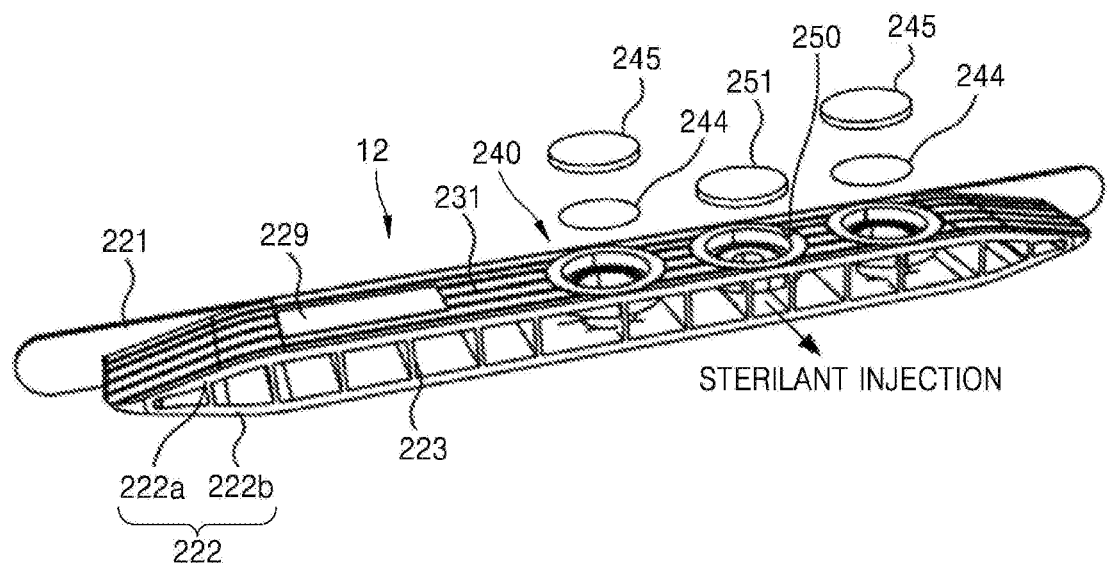
Figure 7D:
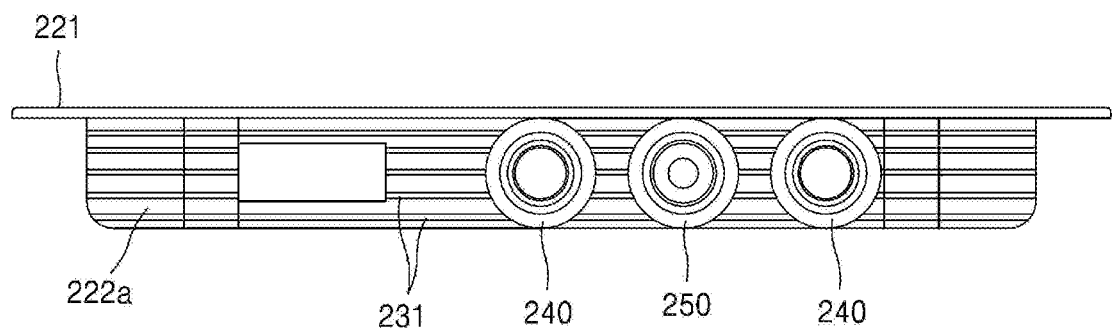
Figure 7E:
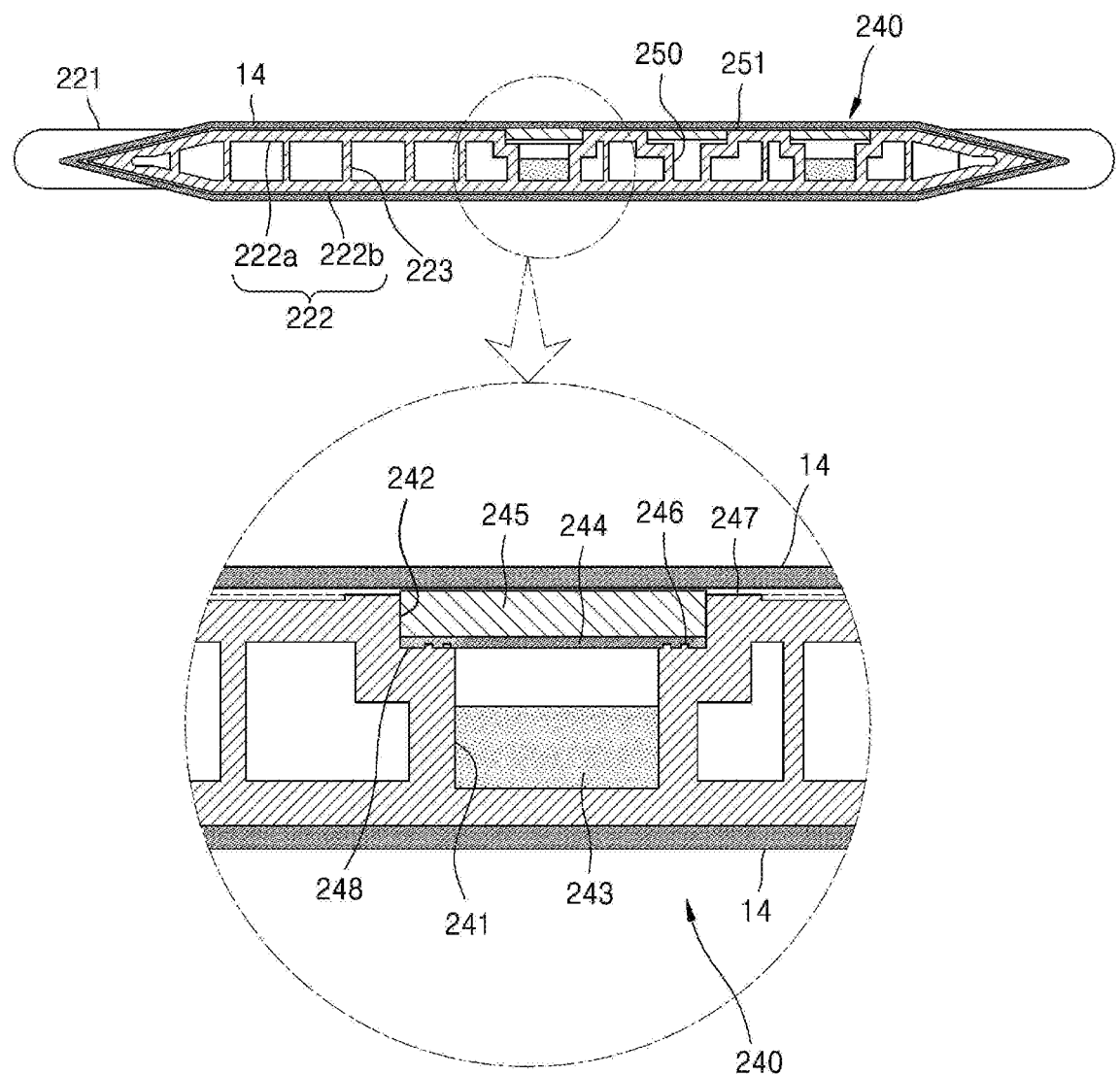

FIG. 6 is a view of an experimental result of displaying a second rate of a change in pressure of FIG. 5 according to the amount of water injected into a sterilization container.

Referring to FIGS. 1 and 2, the residual water diagnostic method includes operation S110 of initially evacuating a sterilization container containing a target object to a vacuum for a first time interval T1; operation S120 of stopping initial evacuation of the sterilization container and calculating a first rate of pressure rise ROR1 in time of the sterilization container for a second time interval T2; operation S130 of performing secondary exhaust of the sterilization container for a third time interval T3 when the first rate of pressure rise ROR1 is within a set range; and operation S14 of stopping the secondary exhaust of the sterilization container and calculating a second rate of pressure rise ROR2 in time of the sterilization container for a fourth time interval T4.

When excessive residual moisture remaining in the sterilization container is removed using a vacuum pump, the residual moisture may reduce the performance and the life of a vacuum pump. In addition, if the residual moisture is different for each target object, sterilization reproducibility may decrease after a sterilization process is completed. Therefore, before proceeding with the sterilization process, the amount of residual moisture remaining in the target object is diagnosed, and appropriate measures such as stopping the sterilization process or adding a drying process are required according to the predicted amount of residual moisture.

In operation S110, the initial evacuation is performed by opening a valve connecting the vacuum pump and the sterilization container. The sterilization container is a sealed vacuum chamber, which may be a sterilization chamber or a vacuum pouch.

When the sterilization container is a vacuum pouch, the vacuum pouch may be disposed inside the vacuum chamber to ensure the volume of the vacuum pouch. The vacuum chamber and the vacuum pouch may be evacuated at the same time.

The first time interval T1 may be 20 seconds to 90 seconds. The first time interval T1 may be at least several times the characteristic time of a vacuum exhaust system. The characteristic time of the vacuum exhaust system may be proportional to the volume of the sterilization container and inversely proportional to the pumping speed of the vacuum pump. By the initial evacuation, the pressure of the sterilization container may be reduced exponentially. After completion of the initial evacuation in operation S110, the pressure of the sterilization container may be at or below vaporization pressure corresponding to a boiling point of water at the temperature of the sterilization container. In more detail, after the initial evacuation at room temperature, the pressure of the sterilization container may be 30 Torr or less, which is the vaporization pressure. After completion of the initial evacuation, residual moisture may be evaporated in a sterilization container maintained at a certain temperature to increase pressure. For example, when the first time interval T1 for performing the initial evacuation is 30 seconds, the sterilization container may reach pressure of 30 Torr or less, and residual moisture may evaporate under the pressure of 30 Torr or less.

The initial evacuation of the sterilization container is stopped and the first rate of pressure rise ROR1 in time of the sterilization container is calculated for the second time interval T2. In more detail, the initial evacuation is stopped by closing the valve connecting the vacuum pump and the sterilization container. The vacuum gauge measures pressure in the sterilization container in time. A set range of the first rate of pressure rise ROR1 may be 0 Torr/sec to 0.2 Torr/sec. Preferably, the set range of the first rate of pressure rise may be 0.04 Torr/sec to 0.1 Torr/sec.

When the first rate of pressure rise ROR1 exceeds the set range, the sterilization container may be vented to atmospheric pressure due to excessive residual moisture. If the first rate of pressure rise ROR1 is less than the set range, the sterilization container may be evacuated through additional pumping due to the absence of residual moisture. The additional pumping may provide initial conditions for the subsequent sterilization process. The second time interval T2 may be 10 seconds to 30 seconds. When the second time interval T2 is less than a few seconds, inaccurate pressure data is detected by initial pressure fluctuation, and when the second time interval T2 is several hundred seconds or longer, a residual water diagnosis time is increased and the vaporization pressure may be decreased by increasing pressure.

According to experimental results of FIGS. 3 and 4, the first rate of pressure rise ROR1 is proportional to the amount of water injected into the sterilization container. When no water is injected, the first rate of pressure rise ROR1 is less than 0.04 Torr/sec. When 0.12 milliliters or more of water is injected, the first rate of pressure rise ROR1 may exceed 0.1 Torr/sec. Therefore, when the first rate of pressure rise ROR1 is measured, the amount of water or residual water injected into the sterilization container may be predicted. The first rate of pressure rise ROR1 may provide quick determination on excessive residual moisture.

When the first rate of pressure rise ROR1 is within a set range, secondary exhaust may be performed during the third time interval T3. The secondary exhaust is performed by opening a valve connecting a vacuum pump and a sterilization container. The third time interval T3 may be at least several times the characteristic time of a vacuum system. The pressure in the sterilization chamber may again decrease exponentially. After the third time interval T3 ends, different pressures may be maintained according to the amount of residual moisture. The third time interval T3 may be 10 seconds to 50 seconds. After the third time interval T3 ends, the pressure of the sterilization container may be 10 Torr or less.

Referring to FIGS. 2, 5, and 6, the lowest pressure is shown when there is no water injected from outside immediately after the third time interval T3 ends.

However, when the amount of injected water is 0.03 milliliters to 0.15 milliliters, the pressures may be difficult to distinguish from each other immediately after the third time interval T3 ends.

The secondary exhaust of the sterilization container is stopped and the second rate of pressure rise ROR2 in time of the sterilization container is calculated during the fourth time interval T4. In more detail, the secondary exhaust is stopped by closing a valve connecting the vacuum pump and the sterilization container. The vacuum gauge measures the pressure in the sterilization container in time. The second rate of pressure rise ROR2 may be greater than the first rate of pressure rise ROR1 due to low base pressure. The second rate of pressure rise ROR2 is proportional to the amount of injected water.

A set range of the second rate of pressure rise ROR2 may be 0.1 Torr/sec to 0.4 Torr/sec. When the second rate of pressure rise ROR2 exceeds the set range, the sterilization container may be vented to atmospheric pressure due to excessive residual moisture. If the second rate of pressure rise ROR2 is less than the set range, the sterilization container may be evacuated through additional pumping due to the absence of residual moisture. The fourth time interval T4 may be 10 seconds to 40 seconds. When the fourth time interval T4 is less than a few seconds, inaccurate pressure data is detected by initial pressure fluctuation, and when the fourth time interval T4 is several hundred seconds or longer, the residual water diagnosis time may be increased.

When the second rate of pressure rise ROR2 is within a set range, the sterilization container may be additionally dried and evacuated to dry the target object. A drying and evacuating time interval may be proportional to the second rate of pressure rise ROR2. After the drying and evacuating process, residual moisture of the target object may be reduced below a reference value to allow for a reliable sterilization process.

If there is excessive moisture under the initial evacuation and the first rate of pressure rise, the process is stopped to maintain the performance of a vacuum device or to ensure process stability. The amount of residual moisture may be accurately predicted under the secondary exhaust and second rate of pressure rise, and a drying and evacuating process may be performed that is proportional to the predicted amount of residual moisture. Accordingly, by performing the optimal drying process in a minimum time, the reliability and processing time of the sterilization process may be shortened The residual water diagnosis process according to an embodiment of the present invention measures pressure reached through the initial evacuation and closes the valve connected to the vacuum pump to measure the first rate of pressure rise ROR1 in an isolated state. The first rate of pressure rise may be used to early determine whether there is excessive moisture inside the target object or the sterilization container. When the first rate of pressure rise ROR1 is 0.1 Torr/sec or more, it may be determined that there is excessive residual moisture.

The residual water diagnosis process according to an embodiment of the present invention measures the first rate of pressure rise ROR1 during the initial evacuation and after the initial evacuation stop, measures pressure reached through the secondary exhaust process again, and measures the second rate of pressure rise ROR2 while the secondary exhaust process is stopped. The second rate of pressure rise ROR2 may be used to accurately predict the amount of residual moisture. Depending on the predicted amount of residual moisture, an optimal drying and evacuating process may proceed.

The first rate of pressure rise ROR1 and/or the second rate of pressure rise ROR2 according to an embodiment of the present invention may be performed by measuring an ROR and curve fitting the amount of residual moisture. When a drying process corresponding to the predicted residual moisture proceeds, reliability of a subsequent sterilization process may be ensured.

According to another aspect of the present invention, a residual water diagnostic method includes evacuating a sterilization container at least once to form a vacuum, and then measuring a rate of pressure rise due to vaporization of moisture remaining in the sterilization container while the evacuation is interrupted and predicting the amount of moisture remaining in a target object. In the residual water diagnostic method, the amount of residual moisture may be predicted by repeating evacuation of the sterilization container and interruption of the evacuation twice.

At atmospheric pressure, water reaches a boiling point at 100° C. and may evaporate quickly. However, when vaporization pressure (about 30 Torr) is formed with a slight vacuum even at room temperature (25° C.), water reaches the boiling point. In this way, a slight vacuum is initially formed to measure the amount of moisture evaporated from a target object to predict residual moisture. In order to primarily predict the amount of residual moisture, initial evacuation is performed at a temperature of the sterilization container at pressure less than or equal to the vaporization pressure. Subsequently, the initial evacuation is stopped in a state where the initial evacuation is completed, and the first rate of pressure rise ROR1 due to the evaporation of residual moisture is measured. The amount of residual moisture is predicted early according to the first rate of pressure rise ROR1. Next, when the amount of residual moisture is within a certain range, secondary exhaust is performed to predict the precise amount of residual moisture. The pressure after completion of the secondary exhaust may be no more than 1/10 of the vaporization pressure at the temperature of the sterilization container. Subsequently, the secondary exhaust is stopped in the state where the secondary exhaust is completed, and a second rate of pressure rise due to evaporation of the residual moisture is measured. According to the second rate of pressure rise ROR2, the amount of residual moisture is again accurately predicted. Accordingly, by measuring vacuum reached pressure and a rate of a change in pressure (or ROR), it is possible to predict residual moisture and provide an optimized drying process.

FIGS. 7A to 7E are conceptual views of a sterilization device according to an embodiment of the present invention.

Referring to FIGS. 7A to 7E, a sterilization pouch sterilization device 100 includes a sterilization pouch 10 having a sterilization packaging bag 14 that is sealed to store a target object therein and to be kept in a vacuum state and a sterilant injection block 12 for containing a sterilant and injecting the sterilant into the sterilization packaging bag 14; a vacuum chamber 120 having a door 124 and accommodating the vacuum pouch; needles 192a, 192b, and 194a for extracting the sterilant contained in the sterilization pouch 10, injecting the extracted sterilant into the sterilization pouch 10, and vacuum evacuating the vacuum pouch; and a vacuum pump 140 for exhausting the sterilization pouch 10 and the vacuum chamber 120.

The sterilant injection block 12 includes a sterilant container 240 sealed to contain the sterilant and a sterilant injection path 250. The sterilization packaging bag 14 is thermocompressed with the sterilant injection block 12 and stores a target object.

The sterilant container 240 includes a sterilant containing space 241 for containing a sterilant 243; a sterilant stopper accommodating space 242 continuously connected to an upper surface of the sterilant containing space 241 and having a larger area than the upper surface of the sterilant containing space 241; a sealing film 244 for sealing an interface between the sterilant containing space 241 and the sterilant stopper accommodating space 242; and a sterilant stopper 245 disposed in the sterilant stopper accommodating space and having elasticity.

The sterilant 243 extracted from the sterilant container 240 is injected into the sterilization packaging bag 14 through the sterilant injection path 250 to sterilize the target object.

The vacuum chamber 120 may include the door 124 and a chamber body 122. The door 124 may be a cover of the vacuum chamber 120. The door 124 may be coupled to the vacuum chamber 120 by a rotating unit such as a hinge. The vacuum chamber 120 may provide an environment in which the sterilization pouch 10 is expanded to secure a constant internal volume by removing a pressure difference between the inside and the outside of the sterilization pouch 10.

The needles 192a, 192b, and 194a may include the auxiliary needles 192a and 192b for extracting a sterilant and the main needle 194a for injecting the extracted sterilant into the vacuum pouch through the sterilant injection path.

The vacuum chamber 120 may have a space for containing the sterilization pouch 10 and a heating block 185 therein. The vacuum chamber 120 may have a rectangular parallelepiped shape and may be formed of metal.

The vacuum chamber 120 may be connected to the vacuum pump 140 through a connection pipe. The vacuum pump 140 may vacuum evacuate the vacuum chamber 120 and the sterilization pouch 10.

A filter 150 may suck in the air to remove fine dust and bacteria and provide the air to the vacuum chamber 120 or the sterilization pouch 10.

A vaporizer 130 may receive the sterilant contained in the sterilization pouch 10 to vaporize the sterilant and inject the sterilant into the sterilization pouch 10. When the sterilant is hydrogen peroxide, the vaporizer 130 may heat and vaporize the sterilant at a temperature of 50° C. to 110° C. and may inject the vaporized sterilant into the sterilization pouch 10. The vaporizer 130 may be disposed outside the vacuum chamber. The vaporizer 130 may be provided with a sterilant of the sterilant container 240 through the auxiliary needles 192a and 192b.

The heating block 185 may be disposed within the vacuum chamber 120 and may contact the sterilant injection block 12 to heat the sterilant injection block 12.

The heating block 185 is heated from 50° C. to 110° C. and may heat some or the entire sterilization pouch 10. The heating block 112 may be mounted on the door 124 of the sterilization chamber and may vertically move to apply pressure to the sterilant injection block 12.

When the vacuum chamber 120 is vacuum evacuated, heat transfer through the air is impossible. Therefore, the heating block 185 may be pressed to directly contact the sterilization pouch 10 or the sterilant injection block 12. The heating block 185 may be in the shape of a rod having a rectangular cross section. The inside of the heating block 185 may be heated by a heating wire. The heating block 112 may press and heat the sterilant injection block 12 of the sterilization pouch 10.

A sterilization pouch support 182 is disposed within the vacuum chamber 120 and may align and support the vacuum packaging pouch 10c. In addition, the sterilization pouch support 182 may have a plate shape and may include a plurality of openings 182a to allow the needles 192a, 192b, and 194a to access the sterilant injection block 12. The sterilization pouch support 182 may include an alignment portion protruding for alignment of the sterilization pouch. The sterilization pouch support 182 is formed of metal or an insulator, and may be heated so as to be maintained at a constant temperature. The sterilization pouch support 182 may be fixed in the vacuum chamber 120. The sterilization pouch support 182 may be used as a lower surface of the vacuum chamber 120. The sterilization pouch support 182 may be disposed inside the vacuum chamber to support the sterilization pouch and provide an opening for main needles through which the main needle 194a can pass. A sealing member 188 on an upper surface of the sterilization pouch support 182 may contact an upper strip 222a of the sterilant injection block 12 to seal around the sterilant container 240 and around the sterilant injection path 250. The sealing member 188 may be an O-ring. A main needle transfer portion includes an auxiliary sealing member which is in contact with a lower surface of the sterilization pouch support 182 around the opening for main needles to perform sealing.

The main needle 194a may be disposed to pass through the opening for main needles of the sterilization pouch support 182. An end of the main needle 194a is obliquely processed like a typical needle, and an opening (not shown) may be formed in a side surface of the end of the main needle 194a. A fluid path may be provided through an opening of the main needle. The main needle 194a may provide a path for exhausting air from the sterilization pouch 10 and may provide a path for supplying a sterilant from the outside to the inside of the sterilization pouch 10. An inner diameter of the main needle 194a may be at least 0.5 mm or more. The inner diameter of the main needle may be sufficiently short and large to provide sufficient conductance for vacuum evacuation. A length of the main needle 194a may be a few centimeters or less and the inner diameter of the main needle 194a may be 0.5 mm or more. A material of the main needle may be metal or a metal alloy. The main needle transfer portion may provide vertical linear motion to the main needle 194a and may be disposed outside the vacuum chamber 120.

The auxiliary needles 192a and 192b may extract the sterilant 243 contained in the sterilization pouch 10. The auxiliary needles 192a and 192b may extract a liquid sterilant contained in the sterilant container 240 of the sterilization pouch. An auxiliary needle transfer portion may provide vertical linear motion to the auxiliary needle and may be disposed outside the vacuum chamber. The auxiliary needle may have the same structure and shape as the main needle.

The sealing member on the upper surface of the sterilization pouch support 182 may contact the upper strip 222a to seal around the sterilant stopper 245 and around a sterilant injection path stopper 251. The sealing member may be an O-ring. The auxiliary needle transfer portion includes an auxiliary sealing member which is in contact with the lower surface of the sterilization pouch support 182 around an opening for auxiliary needles to perform sealing.

The sterilization pouch 10 includes the sterilant injection block 12 having the sterilant container 240 sealed to contain a sterilant and the sterilant injection path 250; and the sterilization packaging bag 14 that is thermocompressed with the sterilant injection block and contains a target object. The sterilant container 240 includes: the sterilant containing space 241 for containing the sterilant; a sterilant stopper accommodating space 242 continuously connected to an upper surface of the sterilant containing space and having a larger area than the upper surface of the sterilant containing space; the sealing film 244 for sealing an interface between the sterilant containing space and the sterilant stopper accommodating space; and a sterilant stopper 235 disposed in the sterilant stopper accommodating space and having elasticity. The sterilant extracted from the sterilant container is injected into the sterilization packaging bag through the sterilant injection path to sterilize the target object.

The sterilization pouch 10 is made of a nylon (NY) and/or PE material having sufficient flexibility and may be in the form of a bag sealed in a film form. The sterilization pouch 10 may include the sterilization packaging bag 14 containing a target object and the sterilant injection block 12 disposed at one end of the sterilization packaging bag 14. The other end of the sterilization packaging bag 14 is initially opened, and after a target object (e.g., a medical device) is inserted, may be sealed by a method such as thermocompression to include a thermocompression bonding strip. The sterilization pouch 10 may include the sterilant injection block 12 for vacuum evacuation and injecting a sterilant from the outside. The sterilization pouch 10 may include at least one sterilant container 240 for containing a fixed amount of sterilant. The sterilant container 240 may be installed in the sterilant injection block 12.

The sterilization packaging bag 14 may be made of polyethylene. The sterilization packaging bag 14 may include a lower film and an upper film which provide an internal space.

The sterilant injection block 12 may include a PE material that is the same material as that of the sterilization packaging bag 14. Accordingly, the sterilant injection block 12 may be sealed with the sterilization packaging bag 14 by thermocompression. The material of a surface of the sterilant injection block 12 may be the same as the material of the sterilization packaging bag. Accordingly, the sterilant injection block 42 may be thermally compressed with the sterilization packaging bag 14 to provide a sealed space.

The sterilant container 240 includes: the sterilant containing space 241 for containing the sterilant; the sterilant stopper accommodating space 242 continuously connected to the upper surface of the sterilant containing space 241 and having a larger area than the upper surface of the sterilant containing space; the sealing film 244 for sealing an interface between the sterilant containing space 241 and the sterilant stopper accommodating space 242; and the sterilant stopper 245 disposed in the sterilant stopper accommodating space and having elasticity. The sterilant 243 extracted from the sterilant container by an auxiliary needle is injected into the sterilization packaging bag 14 through the main needle and the sterilant injection path 250 to sterilize the target object.

The sterilant injection block 12 may include: an upper strip 222a and a lower strip 222b having opposite ends bent to contact each other and the central portions extending parallel to each other; a barrier wall 223 between the upper strip and the lower strip; the sterilant injection path stopper 251 on the upper strip to block the sterilant injection path 250; and an alignment strip 221 extending laterally along one side of the upper strip 222a and the lower strip 222b to seal the one side of the upper strip and the lower strip. The sterilant injection path 250 penetrates through the upper strip 222a and is exposed to the opposite side of the alignment strip 221, and the sterilant container 240 may be recessed in an upper surface of the upper strip 222a and disposed between the upper strip 222a and the lower strip 222b. The upper surface of the upper strip 222a and a lower surface of the lower strip 222b may be thermocompressed with each other at one end of the sterilization packaging bag.

The sterilant stopper 245 and the sterilant injection path stopper 251 may be made of an elastic material such as silicone rubber. The sterilant stopper 245 and the sterilant injection path stopper 251 may be fixed by fitting and/or an adhesive.

Thus, even when the needle punctures the sterilant stopper 245 and the sterilant injection path stopper 251 and then retreats, the sterilant stopper 245 and the sterilant injection path stopper 251 may sufficiently seal the sterilization pouch. After the sterilization process is completed, even when the sterilization pouch is exposed to the polluted atmosphere for a long time, the sterilant injection path stopper 251 may prevent infiltration of bacteria. The sterilant stopper 245 may suppress leakage of the remaining sterilant. An upper surface of the sterilant stopper 245 and the sterilant injection path stopper 251 may protrude about 0.1 mm from the upper surface of the upper strip 222a. When the sterilization packaging bag and the upper strip 222a are thermocompressed with each other, the sterilization packaging bag may apply pressure to the sterilant stopper 245. Accordingly, sealing ability of the sterilant stopper 245 may be improved.

The main needle 194a may puncture the sterilant injection path stopper 251. A material of the sterilant injection path stopper 251 may be silicone rubber or an elastic polymer material. When the main needle 194a punctures the sterilant injection path stopper 251, the sterilant injection path stopper 251 may maintain a sealed state by elasticity. When fluid flows through the main needle 194a, the fluid may not leak through the sterilant injection path stopper 251. In addition, when exhausting the inside of the sterilization pouch through the main needle 194a, the sterilant injection path stopper 251 may maintain sufficient vacuum sealing.

The sterilant containing space 241 for containing the sterilant may be a space disposed adjacent to the lower strip 222b between the upper strip 222a and the lower strip 222b. The sterilant containing space 241 may be cylindrical in shape.

The sterilant stopper accommodating space 242 may be a space disposed adjacent to the upper strip 222a. The sterilant stopper accommodating space 242 may be aligned vertically with the sterilant containing space 241 and have a larger cross-sectional area.

When the sterilant containing space 241 is sealed with only a sterilant stopper made of an elastic material, hydrogen peroxide contained in the sterilant containing space 241 may expand and leak from a gap between the sterilant stopper 245 and the sterilant stopper accommodating space 242 to peel off the thermocompressed sterilization pouch. In order to solve this problem, the sealing film 244 may seal the interface between the sterilant containing space 241 and the sterilant stopper accommodating space 242. The sealing may be performed by thermocompression. For efficient thermocompression sealing, the sealing film 244 may be the laminated film of the PE film/PET film. The PE film of the sealing film 244 may be thermocompression-bonded to a lower surface of the sterilant stopper accommodating space 242 of a PE material. The lower surface of the sterilant stopper accommodating space 242 may have a protruding thermocompression ring 246 in the form of a ring.

Each of the upper strip 222a and the lower strip 222b may include a plurality of thermocompression lines 231 extending in a length direction and protruding from the surface thereof.

The thermocompression lines 231 may perform efficient thermocompression with the sterilization packaging bag 14.

The height of the upper strip 222a around an upper surface of the sterilant stopper accommodating space 242 may be equal to the height of the thermocompression lines 231. Accordingly, the sterilization packaging bag 14 may be efficiently thermocompressed around the upper surface of the sterilant stopper accommodating space 242.

In addition, the height of the upper strip 222a around an upper surface of the sterilant injection path 250 may be the same as the height of the thermocompression lines 231. As a result, the sterilization packaging bag 14 may be efficiently thermocompressed around the upper surface of the sterilant injection path 250.

A code adhesive tape 229 having code such as a bar code or a QR code to be printed may be attached to the sterilization pouch 10 or the sterilant injection block 12. It is possible to perform a reliable sterilization process by transmitting information about the amount of sterilant injected by using the code adhesive tape 229, the type of packaging container, date of manufacture, etc. to the sterilizer. A code reader 184 may extract information of the code adhesive tape 229 through an opening formed in a vacuum pouch supporter 182.

The sterilization pouch sterilization device 100 may include a plurality of valves 161 to 166. The valves 161 to 166 may be used to evacuate the sterilization pouch 10 and the vacuum chamber 120, to inject a sterilant into the sterilization pouch, and to vent the sterilization pouch and the vacuum chamber to the atmosphere.

A first pressure gauge 31 may measure pressure of the vacuum chamber 120, and a second pressure gauge 32 may measure pressure of the sterilization pouch 10.

Pressure P1 of the first pressure gauge 31 and pressure P2 of the second pressure gauge 32 are provided to a controller 189, and the controller 189 may calculate the first rate of pressure rise ROR1 and the second rate of pressure rise ROR2 by using a change in pressure in the second pressure gauge 32. The controller may control the sterilization pouch sterilization device 100 using the first rate of pressure rise and/or the second rate of pressure rise to perform a residual water diagnosis process and a sterilization process.

Using a sterilant such as hydrogen peroxide, a sterilization process of a target object (sterilization load) is performed. A vaporizer vaporizes hydrogen peroxide and the hydrogen peroxide is exposed to the target object. Accordingly, chemical sterilization is performed by inactivation through oxidation of cell walls and nuclei of microorganisms remaining in the target object.

[Preparation of Target Object]

Packaging is required to maintain suitability of a sterilization process for sterilization by exposing a sterilant to a target object and sterile conditions until the time when the sterilized target object is used. The target object may be washed, dried and packaged through a sterilization pouch. The target object may be washed with water or a cleaning agent, and the drying may be drying by pressurized air, natural drying at atmospheric pressure, or hot air drying by hot air. Moisture remaining on the surface of the target object cannot guarantee sterilization performance, so sufficient drying of the target object is required.

[Residual Water Diagnosis Process]

The target object may include residual moisture remaining in washing and predrying processes. The target object is stored in the sterilization pouch, and the residual water diagnosis process is performed before a sterilization process. The sterilization container may be a sterilization pouch. The target object may be a medical device.

Figure 8:
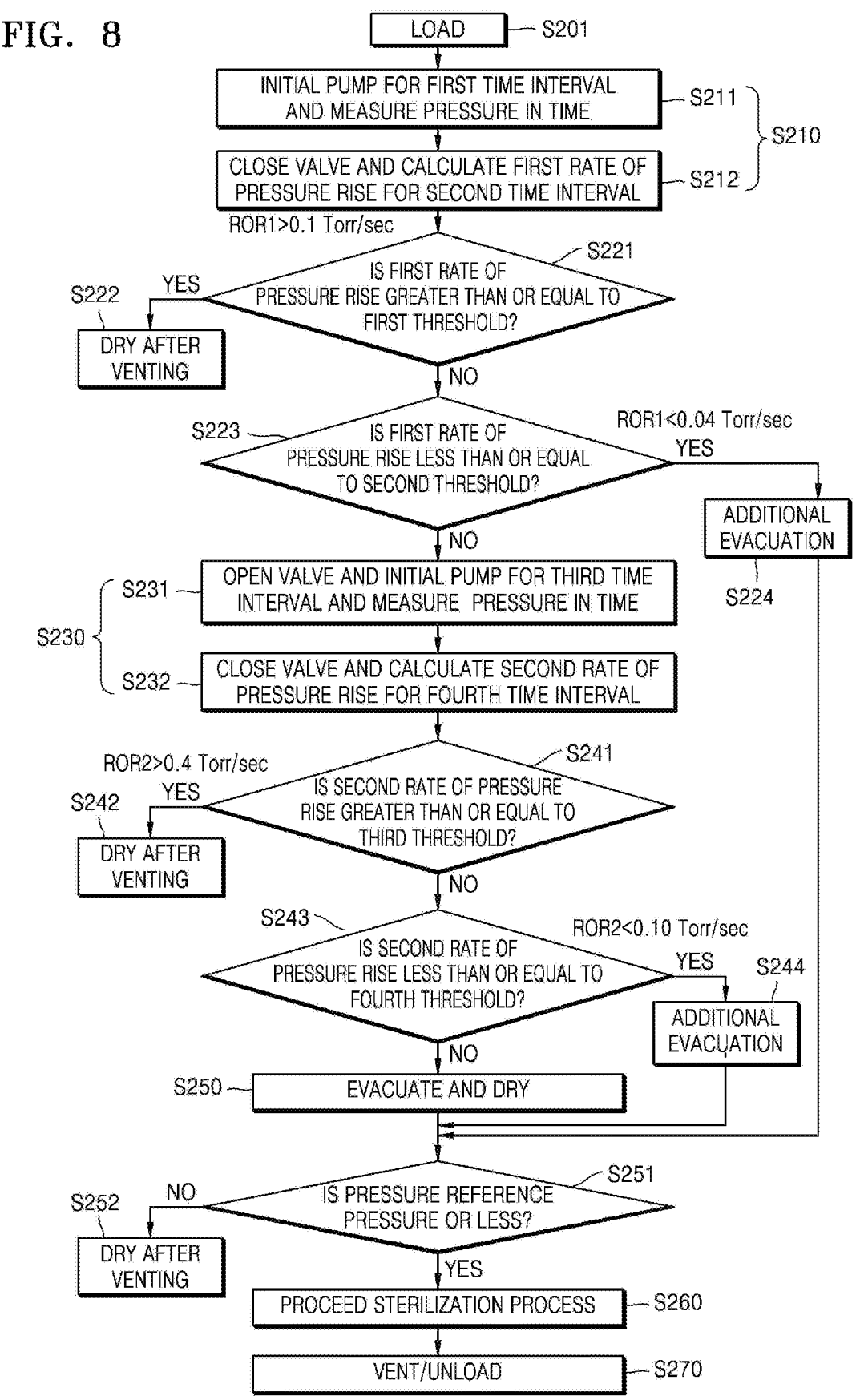
FIG. 8 is a flowchart illustrating a sterilization process according to an embodiment of the present invention.

FIG. 8 is a flowchart illustrating a sterilization process according to an embodiment of the present invention.

Figure 9:
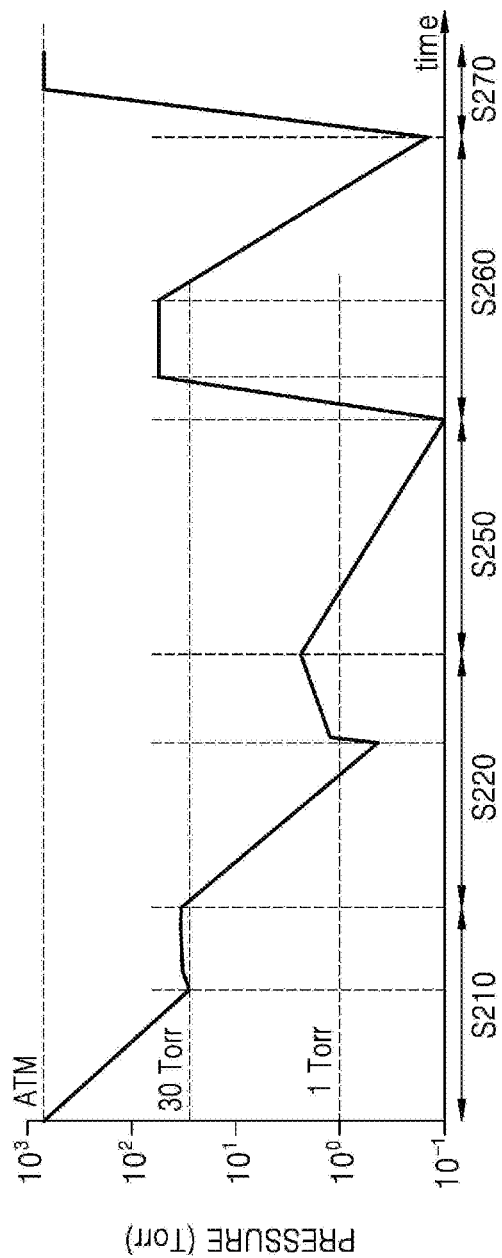
FIG. 9 is a view of the pressure of a sterilization pouch according to the sterilization process of FIG. 8.

FIG. 9 is a view of the pressure of a sterilization pouch according to the sterilization process of FIG. 8.

Referring to FIGS. 7 to 9, the sterilization method according to an embodiment of the present invention includes operation S210 of, after initial sterilization of the sterilization pouch 10 containing a target object to a vacuum for the first time interval T1, stopping the initial evacuation of the sterilization pouch 10 and calculating the first rate of pressure rise ROR1 in time of the sterilization pouch 10; and operation S220 of sterilizing the sterilization pouch 10 by injecting a sterilant into the sterilization pouch 10.

In operation S210, the sterilization pouch 10 is loaded into the vacuum chamber 120. The sterilization pouch 10 may include a vacuum pouch.

The sterilization pouch 10 containing a target object is initially evacuated for the first time interval T1 in a vacuum. In operation S211, the vacuum chamber 120 and the sterilization pouch 10 may be evacuated to a vacuum at the same time. In order to evacuate the vacuum chamber 120, the first valve 161 and the sixth valve 166 may be opened. In addition, the main needle 194*a* may pierce the sterilization pouch 10 and open the fourth valve 164 to exhaust the sterilization pouch 10. The evacuation of the vacuum chamber 120 may be performed to ensure the volume of the sterilization pouch 10. After the initial evacuation, the pressure of the sterilization pouch 10 may be equal to or less than the vaporization pressure (about 30 Torr) corresponding to a boiling point based on room temperature.

In operation S212, the initial evacuation of the sterilization pouch 10 is stopped and a first rate of pressure rise in time of the sterilization pouch 10 is calculated for the second time interval T2. The stopping of the initial evacuation of the sterilization pouch 10 may be performed by closing the sixth valve 166. The first valve 161 may also be closed at the same time when the initial evacuation is stopped.

During the second time interval T2, residual moisture is vaporized to increase the pressure of the sterilization pouch 10. The first rate of pressure rise ROR1 of the sterilization pouch 10 may depend on the amount of residual moisture.

In operation S222, when the first rate of pressure rise is greater than or equal to a first threshold, the sterilization pouch 10 may be vented to the atmosphere. The venting of the sterilization pouch 10 may be performed by closing the sixth valve 166 and opening the fifth valve 165 and the fourth valve 164. When the sterilization pouch 10 is vented to the atmosphere, the vacuum chamber 120 may also be vented to the atmosphere. The venting of the vacuum chamber 120 may be performed by opening the first valve 161. The first threshold may be 0.1 Torr/sec. At the first rate of pressure rise ROR1 equal to or greater than the first threshold, the process may be stopped due to excessive residual moisture.

In operation S223, when the first rate of pressure rise ROR1 is less than the first threshold and less than or equal to a second threshold, additional exhaust may be performed even if the residual moisture is less in operation S224. The second threshold may be 0.04 Torr/sec. The additional exhaust may exhaust the sterilization pouch 10 to reference pressure (e.g., 1 Torr) or less, thereby satisfying conditions under which a sterilization process is to be performed. The vacuum chamber 120 may also be evacuated at the same time during the additional evacuation.

In operation S230, after the first rate of pressure rise ROR1 is calculated and then the sterilization pouch 10 is secondarily evacuated in a vacuum for the third time interval T3, the secondary exhaust of the sterilization pouch 10 is stopped, and a second rate of pressure rise in time of the sterilization pouch 10 may be calculated.

Operation S231 of the secondary exhaust of the sterilization pouch 10 to a vacuum for the third time interval T3 may be performed as in the vacuum chamber 120. After completing the secondary exhaust of the sterilization pouch 10, the pressure of the sterilization pouch 10 may be $\frac{1}{10}$ or less of the vaporization pressure at room temperature.

In operation S232, the second exhaust of the sterilization pouch 10 may be stopped and residual moisture may be evaporated during the fourth time interval T4 to increase the pressure. The second rate of pressure rise ROR2 may be greater than the first rate of pressure rise ROR1 for the same amount of residual moisture.

The calculation of the second rate of pressure rise ROR2 may be performed when the first rate of pressure rise is within a certain range. That is, the calculation of the second rate of pressure rise ROR2 may be performed within a range in which the first rate of pressure rise is 0.04 Torr/sec to 0.1 Torr/sec.

In operation S241, when the second rate of pressure rise ROR2 is greater than or equal to a third threshold, then in operation S242, the sterilization pouch 10 may be vented to the atmosphere. The third threshold may be 0.4 Torr/sec.

In operation S243, when the second rate of pressure rise ROR2 is less than or equal to a fourth threshold, then in operation S244, additional exhaust may be performed. The fourth threshold may be 0.1 Torr/sec.

In operation S250, when the second rate of pressure rise ROR2 is within a certain range, the sterilization pouch 10 may be evacuated and dried to dry the target object. The certain range of the second rate of pressure rise may be 0.01 Torr/sec to 0.4 Torr/sec. The time for the evacuating and drying may be proportional to the second rate of pressure rise ROR2. In operation S243, the evacuating and drying time may be greater than an additional evacuation time when the evacuating and drying time is less than or equal to the fourth threshold.

After the evacuating and drying in operation S250 or the additional evacuating in operations S224 and S244, when the pressure of the sterilization pouch 10 is greater than reference pressure in operation S251, in operation S252, the sterilization pouch 10 may be vented to the atmosphere.

After the evacuating and drying in operation S250 or the additional evacuating in operations S224 and S244, when the pressure of the sterilization pouch 10 is the reference pressure or less in operation S251, in operation S260, a sterilization process may proceed.

A sterilization device may perform a sterilization process using a vacuum pouch.

A needle is connected to a silicone pad portion of the vacuum pouch to supply a sterilant directly into the vacuum pouch. After the sterilization process is completed, the needle is removed and the pouch composed of an impermeable film may be completely sealed. Accordingly, sterility preservation may be ensured. The sterilant may use the vacuum pouch itself as a cassette using a hydrogen peroxide solution stored in the vacuum pouch.

Hydrogen peroxide needs to be exposed to a target object in a gas phase during the sterilization process. To this end, a sufficient vacuum (3 Torr or less) is formed initially and the target object needs to be heated to a temperature sufficient to prevent condensation of a gaseous sterilant at the pressure (about 50 Torr) at which the sterilant is injected and diffused. The temperature rise of the target object may be performed during the drying and evacuating process in operation S250 or during the additional evacuation processes in operations S224 and S244. In operation S260, the sterilization process may repeat the same sterilant injection and sterilant evacuation twice for perfect sterilization (overkill method).

According to a modified embodiment of the present invention, the sterilant may be supplied to a sterilization space after the hydrogen peroxide solution stored in a separate cassette is extracted using a needle and vaporized in a vaporizer.

In operation S270, after completion of the sterilization process, the sterilization pouch 10 and the vacuum chamber may be vented and the sterilization container may be unloaded.

Figure 10:
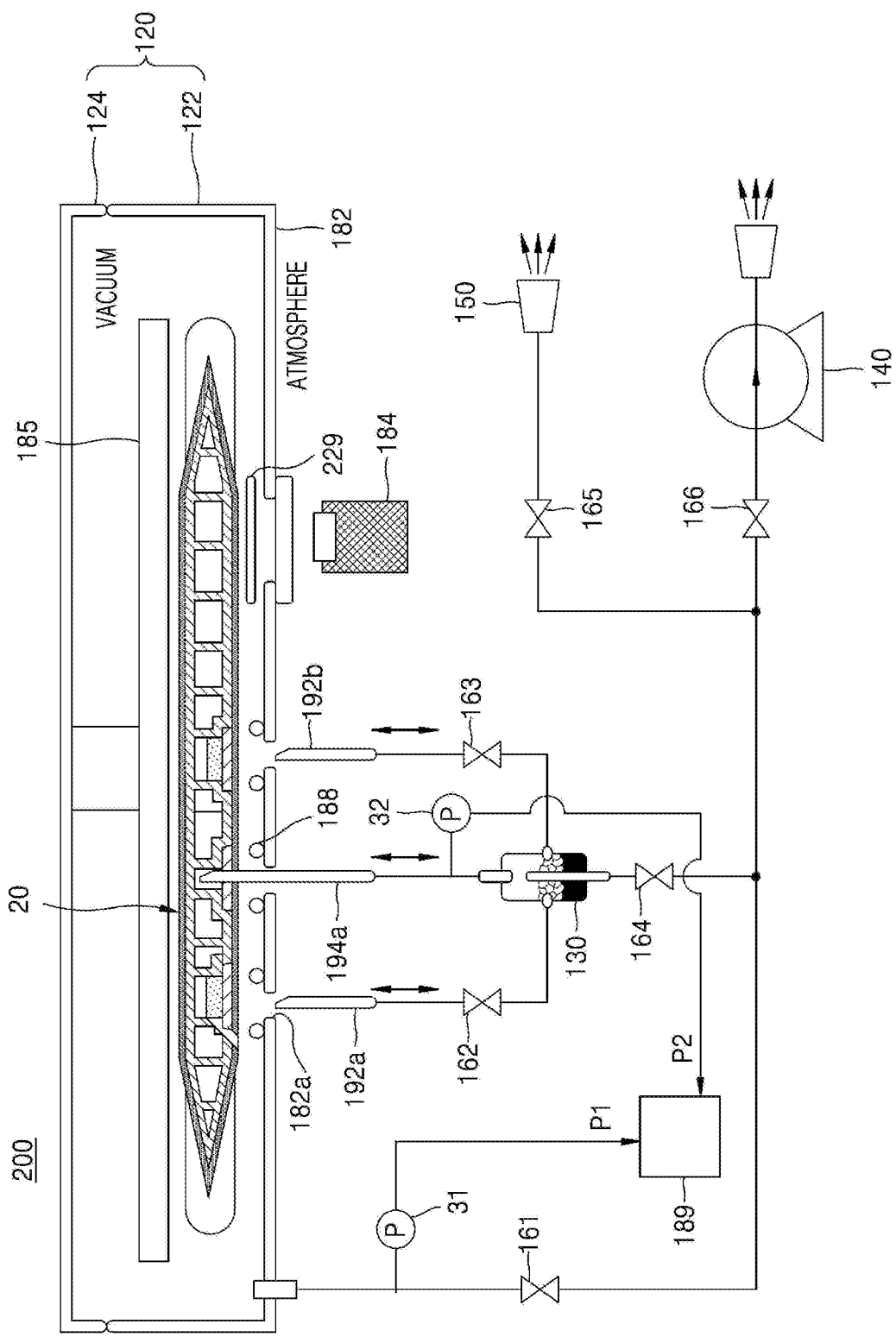
FIG. 10 is a conceptual diagram of a sterilization device according to another embodiment of the present invention.

FIG. 10 is a conceptual diagram of a sterilization device according to another embodiment of the present invention.

Referring to FIG. 10, the sterilization device includes the vacuum chamber 120, and a sterilant cassette 20 disposed in the vacuum chamber 120 and containing a sterilant and injecting the sterilant into the vacuum chamber; and the vacuum pump 140 for evacuating the vacuum chamber 120. The vacuum chamber 120 may be sealed to store a target object therein and to be maintained in a vacuum state. The needles 192a, 192b, and 194a extract the sterilant stored in the sterilant cassette 20, and the vaporizer 130 vaporizes the extracted sterilant and injects the sterilant into the vacuum chamber 120.

A sterilization device 200 may perform a sterilization process by using a nonwoven pouch for packaging a target object. A nonwoven film may sterilize an object therein by passing a sterilant and may ensure sterility preservation by not passing microorganisms. In order to proceed with the process in a chamber mode, the sterilant is stored in the sterilant cassette 20, and the sterilant cassette 20 may be loaded into the vacuum chamber 120. The sterilant cassette 20 may have substantially the same structure as that of the sterilant injection block 12.

The target object may include residual moisture remaining in washing and predrying processes. The target object is packaged in the nonwoven pouch in the vacuum chamber 120 and then stored, and a residual water diagnosis process is performed before the sterilization process. A sterilization container may be the vacuum chamber 120. The first pressure gauge 31 or the second pressure gauge 32 measures the pressure inside the vacuum chamber 120. A processor 189 calculates a rate of pressure rise of the vacuum chamber by measuring pressure of the first pressure gauge 31 or pressure of the second pressure gauge 32 in an exhaust stop state.

The sterilization method or the residual water diagnostic method according to an embodiment of the present invention includes operation S210 of, after initial sterilization of the vacuum chamber 120 containing a target object to a vacuum for a first time interval, stopping the initial evacuation of the vacuum chamber 120 and calculating a first rate of pressure rise in time of the vacuum chamber 120; and operation S220 of sterilizing the vacuum chamber 120 by injecting a sterilant into the vacuum chamber 120. In operation S230, after the first rate of pressure rise ROR1 is calculated and then the sterilization pouch 10 is secondarily evacuated in a vacuum for the third time interval T3, the secondary exhaust of the vacuum chamber 120 is stopped, and a second rate of pressure rise in time of the vacuum chamber 120 may be calculated. The same applies to the residual moisture diagnostic method described above, except that the sterilization container is a vacuum chamber.

Figure 11:
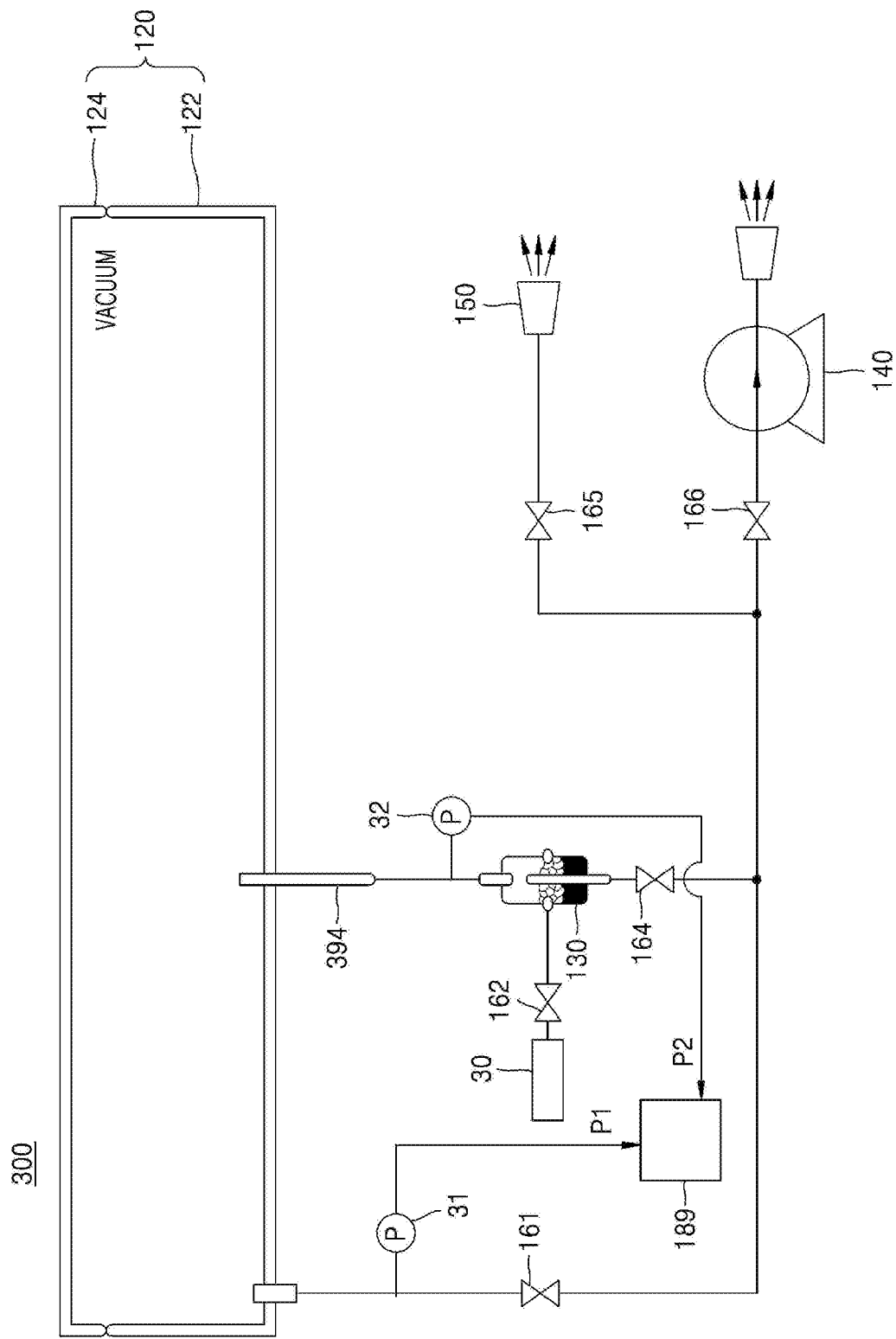
FIG. 11 is a conceptual diagram of a sterilization device according to another embodiment of the present invention.

FIG. 11 is a conceptual diagram of a sterilization device according to another embodiment of the present invention.

Referring to FIG. 11, a sterilization device 300 includes the vacuum chamber 120 and a sterilant cassette 30 disposed outside the vacuum chamber and storing a sterilant; and the vacuum pump 140 for evacuating the vacuum chamber 120. The vacuum chamber 120 may be sealed to accommodate a target object therein and to be maintained in a vacuum state. The sterilant contained in the sterilization cassette 30 is extracted by a sterilant extraction unit such as a needle and vaporized through the vaporizer 130, and then injected into the vacuum chamber 120 through a sterilant injection port 394.

The sterilization device 300 may perform a sterilization process by using a nonwoven pouch for packaging a target object. A nonwoven film may sterilize an object therein by passing a sterilant and may ensure sterility preservation by not passing microorganisms.

In order to proceed with the process in a chamber mode, the sterilant may be stored in a sterilant cassette disposed outside a sterilization chamber.

A target object may include residual moisture remaining in washing and predrying processes. The target object is packaged in the nonwoven pouch in the vacuum chamber and then stored, and a residual water diagnosis process is performed before the sterilization process. A sterilization container may be a vacuum chamber.

The first pressure gauge 31 or the second pressure gauge 32 measures the pressure inside the vacuum chamber 120. A processor 189 calculates a rate of pressure rise of the vacuum chamber by measuring pressure of the first pressure gauge 31 or pressure of the second pressure gauge 32 in an exhaust stop state.

The residual water diagnostic method or the sterilization method according to an embodiment of the present invention includes operation S210 of, after initial sterilization of the vacuum chamber 120 containing a target object to a vacuum for a first time interval, stopping the initial evacuation of the vacuum chamber 120 and calculating a first rate of pressure rise in time of the vacuum chamber 120; and operation S220 of sterilizing the vacuum chamber 120 by injecting a sterilant into the vacuum chamber 120. In operation S230, after the first rate of pressure rise ROR1 is calculated and then the sterilization pouch 10 is secondarily evacuated in a vacuum for the third time interval T3, the secondary exhaust of the vacuum chamber 120 is stopped, and a second rate of pressure rise in time of the vacuum chamber 120 may be calculated. The same applies to the residual water diagnostic method described above, except that the sterilization container is a vacuum chamber and a separate sterilization cassette 30 is installed.

Figure 12:
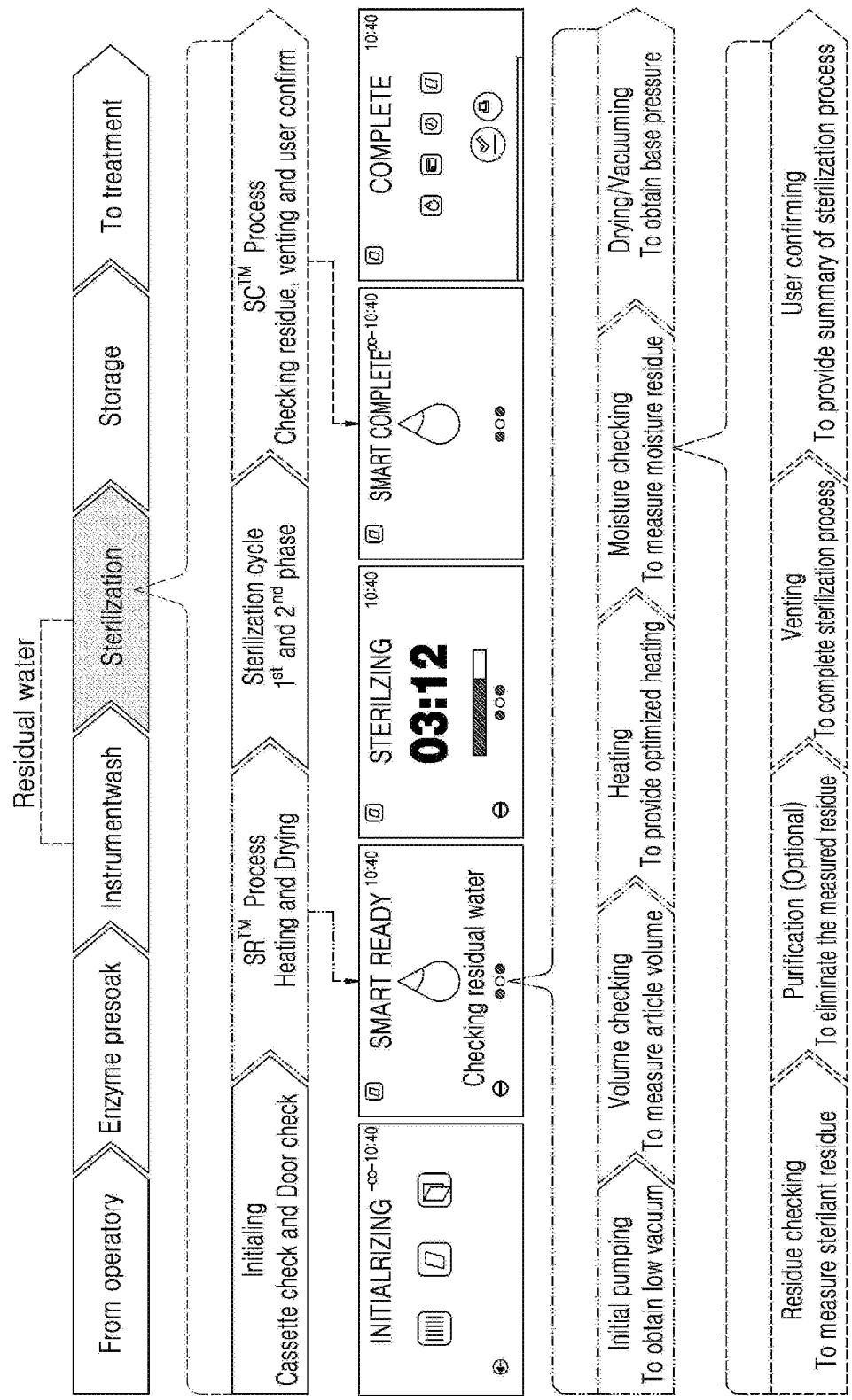
FIG. 12 is a flowchart of sterilization procedure and a view of graphical user interface (GUI) according to the present invention, as an example according to the present invention.

FIG. 12 is a flowchart of sterilization procedure and a view of graphical user interface (GUI) according to the present invention, as an example according to the present invention.

In general, medical instruments used in an operating room or an operatory may be first subjected to enzyme presoak, instrument wash, sterilization, storage, and then used again for surgery or treatment.

The sterilization procedure is further subdivided into initializing a cassette and a locking device such as a chamber or a sealed container, heating and drying the cassette (referred to as an SR process), a sterilization cycle, residue checking, venting, and user confirming (the residue checking and user confirming are collectively referred to as an SC Process).

The SR process is subdivided into: initial pumping to prepare a low level vacuum; checking an effective volume of a sterilized article; heating an impermeable sealed container and the chamber; checking residual moisture; and drying and vacuuming to obtain base pressure.

The SC process is subdivided into: a sterilization cycle, residue check, purification, venting, and user confirming.

[SR Process]

Figure 13:
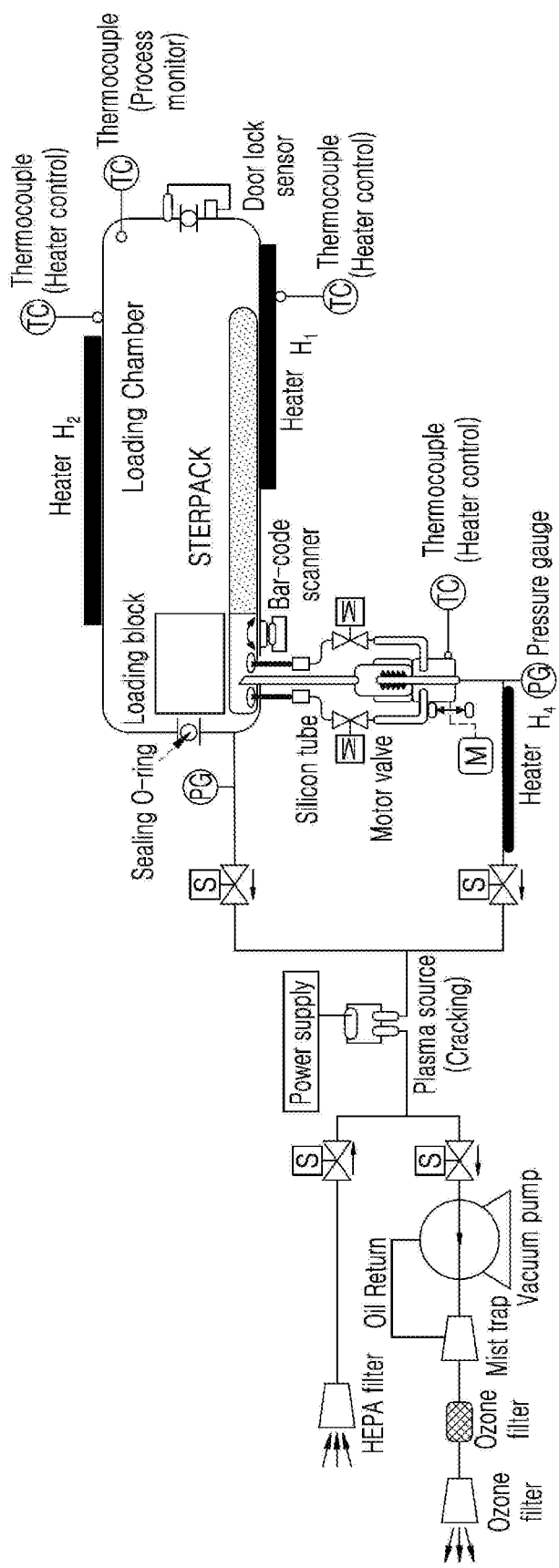
FIG. 13 is a schematic view of a sterilizer as an example according to the present invention.

To illustrate this in more detail, as an example according to the present invention, a schematic view of a sterilizer is illustrated in FIG. 13.

According to the present invention, a vaporizer is directly connected to an impermeable sealed container, and a sterilant and air may be directly supplied through the vaporizer, and a vacuum may be formed.

In addition, the impermeable sealed container is flexible and elastic, so the volume is free to contract and expand according to external pressure, and the air is supplied through the vaporizer to increase the heating efficiency inside the impermeable sealed container.

The vaporizer may be connected to a vacuum pump and an exhaust port to perform independent pressure control through a valve, and may be directly connected to the impermeable sealed container to perform pressure control simultaneously.

In addition, the vacuum pump and the exhaust port are connected together to a plasma source or a catalyst for purifying a sterilant.

In the initial pumping and volume check of the "SR process", it is possible to measure a time to reach a specific value by measuring a pressure value of the impermeable sealed container through a relationship between the pressure value of the impermeable sealed container and the corresponding time.

Figure 14:
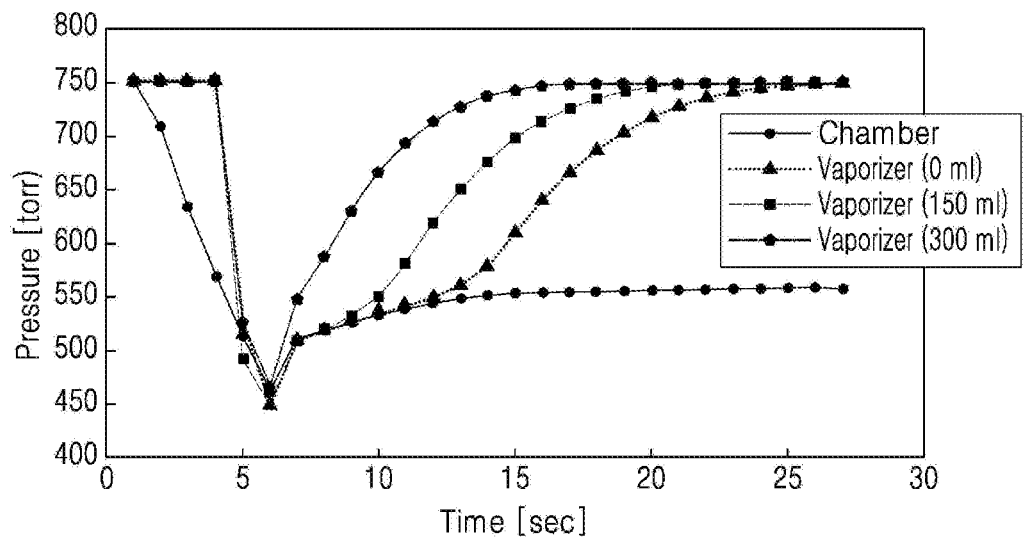
FIG. 14 is a view of a relationship between a pressure value of a closed chamber and the corresponding time in initial pumping and volume check of a sterilization procedure, as an example according to the present invention.

For example, as shown in FIG. 14, an initial value is 750 torr and the initial pumping process from 0 to 6 seconds lowers the pressure to 450 torr to create a low vacuum. The pressure then rises again to determine a time to reach a specific pressure value (650 torr). In the case of 0 ml, it can be seen that 650 torr has been reached in about 16 seconds, and in the case of 150 ml, it can be seen that 650 torr has been reached in about 13 seconds, and the case of 300 ml, it can be seen that 650 torr has been reached in less than 10 seconds (after drawing a horizontal line in a portion corresponding to 650 torr in FIG. 14, see a time axis value at an intersection with a pressure change graph in time).

As such, by measuring the pressure value of the impermeable sealed container, it is possible to obtain a time to reach a specific pressure value. Since the time taken to reach the specific pressure value is a time taken to fill the interior of the impermeable sealed container with air, the time taken to reach the specific pressure value is inversely proportional to a volume of a sterilized article in the impermeable sealed container (i.e., a time required is proportional to a difference between the total volume of a pouch and the volume of the sterilization article, and the more sterilization articles are added, the shorter the time required).

In addition, in order to determine whether the impermeable sealed container is poorly laminated, a relationship between a pressure value between the impermeable sealed container and the chamber and the corresponding time is derived. For example, the interior of the impermeable sealed container is inflated by a pressure difference with the inside of the chamber when continuously venting the inside of the chamber at relatively low pressure (e.g., 550 torr). When a lamination state of the impermeable sealed container is poor or damaged, the pressure difference between the chamber and the impermeable sealed container is reduced (i.e., even if the pressure of the impermeable sealed container is low, when the pressure in the chamber decreases according to Boyle's law, the volume of the impermeable sealed container becomes large. However, when the lamination state is poor and the air in the impermeable sealed container leaks into the chamber, that is, the outside of the impermeable sealed container, there is no pressure difference).

Figure 15:
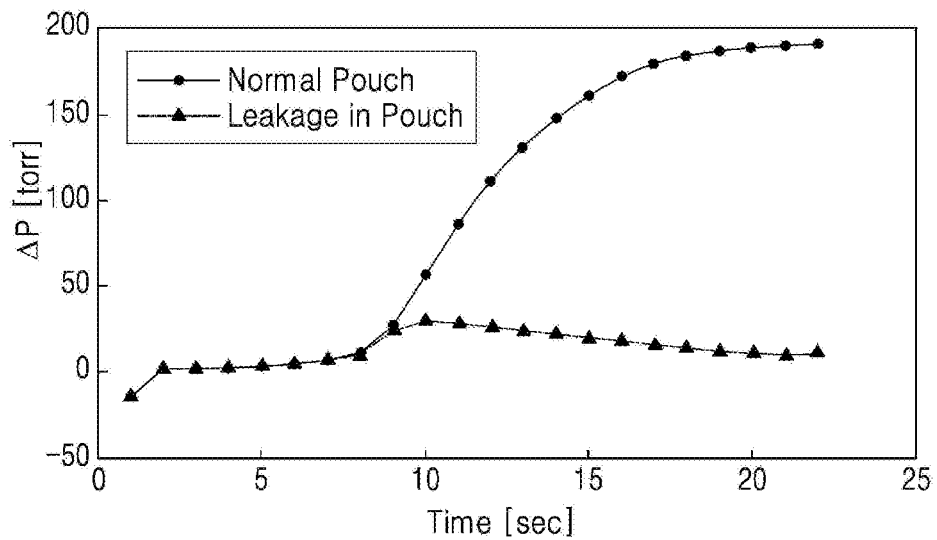
FIG. 15 is a view of a relationship between a pressure value between an impermeable sealed container and a chamber and the corresponding time to determine whether the impermeable sealed container is poorly laminated, as an example according to the present invention.

FIG. 15 illustrates this in more detail. In normal cases, a pressure value P between the impermeable sealed container and the chamber starts from 0 torr in time and rises rapidly around 7 to 8 seconds, and increases to about 200 torr after 20 seconds. On the other hand, when the lamination is poor or damaged, the pressure value P starts from 0 torr, increases slightly around 10 seconds and then decreases again to remain only slightly above the initial 0 torr overall.

Figure 16:
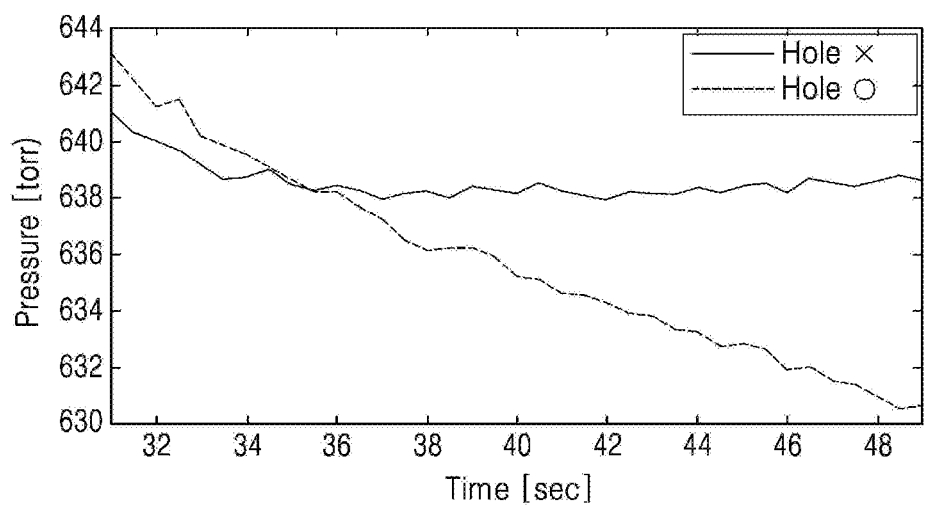
FIGS. 16 and 17 are views of blocking air injection to check sealing errors or tears in an impermeable sealed container during volume check and pouch check, and measuring a relationship between time and pressure for measuring internal pressure of the impermeable sealed container and an hourly rate of a change in pressure inside the impermeable sealed container.
Figure 17:
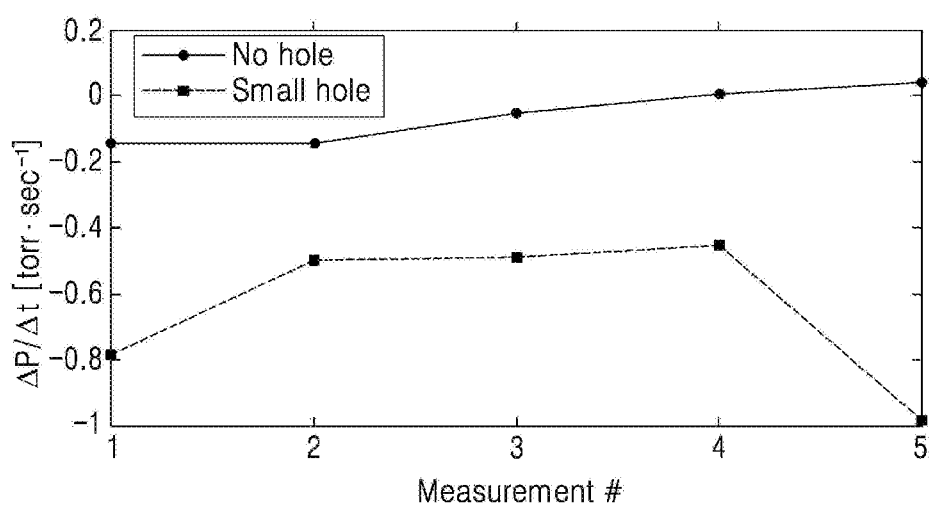

FIGS. 16 and 17 illustrate blocking of air injection to check sealing errors or tears in an impermeable sealed container during volume check and poor lamination check in the "SR process" of the present invention, and measuring of a relationship between time and pressure for measuring internal pressure of the impermeable sealed container and an hourly rate of a change in pressure of the impermeable sealed container.

FIG. 16, which is to check whether the air inside the impermeable sealed container flows into the chamber after measuring an effective volume of a sterilized article and blocking all channels, shows that when there is a lamination error or damage in the impermeable sealed container, the air inside the impermeable sealed container is discharged outward to decrease the pressure, but the pressure is maintained when the impermeable sealed container is normally laminated.

FIG. 17 illustrates a relationship between a rate of a change in pressure inside the impermeable sealed container and the number of measurements per unit time and shows that when the rate of a change in pressure inside the impermeable sealed container per unit time is less than or equal to a specific value (e.g., $-0.4$ torr/sec), the process is stopped by determining that there is a lamination error or tears in the impermeable sealed container (i.e., if the pressure of the impermeable sealed container is continuously reduced due to the lamination error or tears, the rate of a change in pressure per unit time generally shows a negative value, and a rate of a change in pressure as a criterion for determining this is $-0.4$ torr/sec).

The present invention checks an effective volume of a sterilized article by measuring the time that air is supplied to an impermeable sealed container, and increases accuracy of the effective volume check by measuring a time at which the pressure inside the impermeable sealed container reaches a specific value. In this case, after a vacuum is formed, a channel between a vaporizer and the impermeable sealed container is opened to match a pressure value, and air is injected into the impermeable sealed container. However, in order to increase the accuracy of the effective volume check, air is repeatedly injected with an air injection time and a holding time.

According to the present invention, the impermeable sealed container may be sufficiently expanded through the holding time to ensure the accuracy of the effective volume check, and the resolution of time may be controlled by adjusting a ratio of the injection time and the holding time.

In addition, the present invention introduces a method of accurately measuring the number of venting cycles until reaching a specific pressure, as non-integer rational numbers, using a median formula.

Meanwhile, each product on the market requires a zero adjustment for each product. After the zero adjustment, a measurement resolution may be up to 5 ml.

Figure 18:
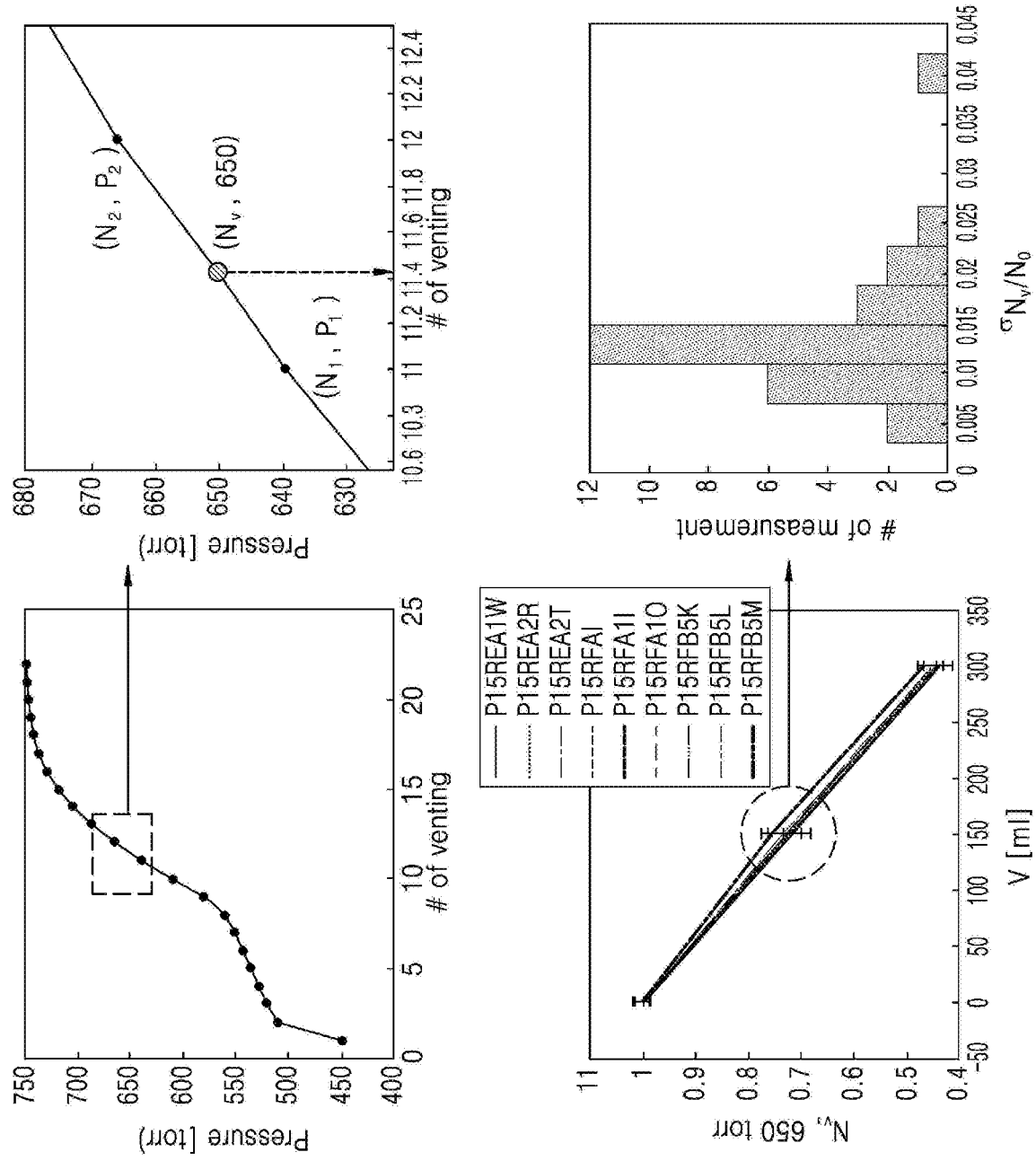
FIGS. 18 and 19 are views showing controlling time resolution by adjusting an air injection time and a holding time during volume check, as an example according to the present invention.
Figure 19:
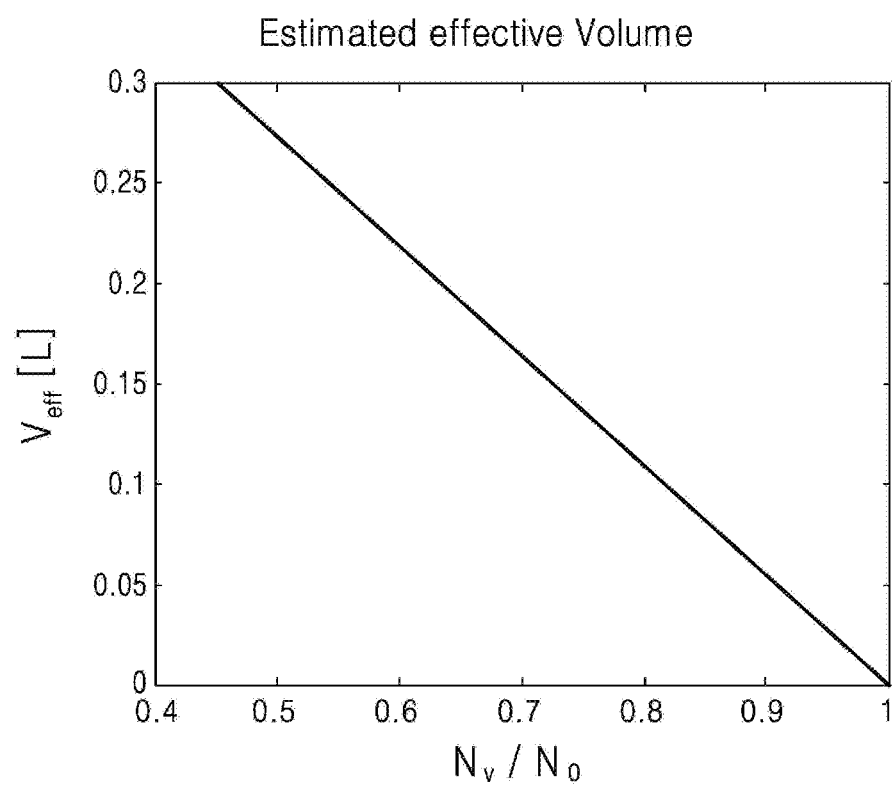

FIGS. 18 and 19 show controlling time resolution by adjusting an air injection time and a holding time during volume checking of the impermeable sealed container to 0.3 seconds and 0.7 seconds respectively, as an example according to the present invention. While measuring a pressure value that changes with the number of venting cycles (# of venting), by drawing a horizontal line corresponding to 650 torr and measuring a horizontal axis value at an intersection with a pressure value graph, the number of venting cycles corresponding to the pressure value can be known (a coordinate value is (Nv, 650) according to FIG. 16). In addition, FIGS. 18 and 19 show graphs showing a relationship between volumes (V, ml) and the number of venting cycles (Nv value) at 650 torr, showing a histogram of the number of measurements and σ Nv/N0 with values at 150 ml. FIGS. 18 and 19 also show a graph showing a relationship between the Nv/N0 and effective volumes (Veff, L) of a sterilized article therefrom.

In the heating of the "SR process" according to the present invention, the inside of the chamber is kept constant at pressure lower than atmospheric pressure so that air inflow into the impermeable sealed container is possible without using a separate device. In addition, the air introduced into the impermeable sealed container is heated through a vaporizer and a pipe to enable efficient temperature raising of a sterilized article, and by using the air introduced into the impermeable sealed container forced convection occurs inside the impermeable sealed container to increase heating efficiency of the sterilized article, wherein the forced convection occurs by repeating exhaust and intake through a pouch-vent line. In addition, a heating time may vary depending on a checked effective volume of the sterilized article, as shown in FIG. 18.

Figure 20:
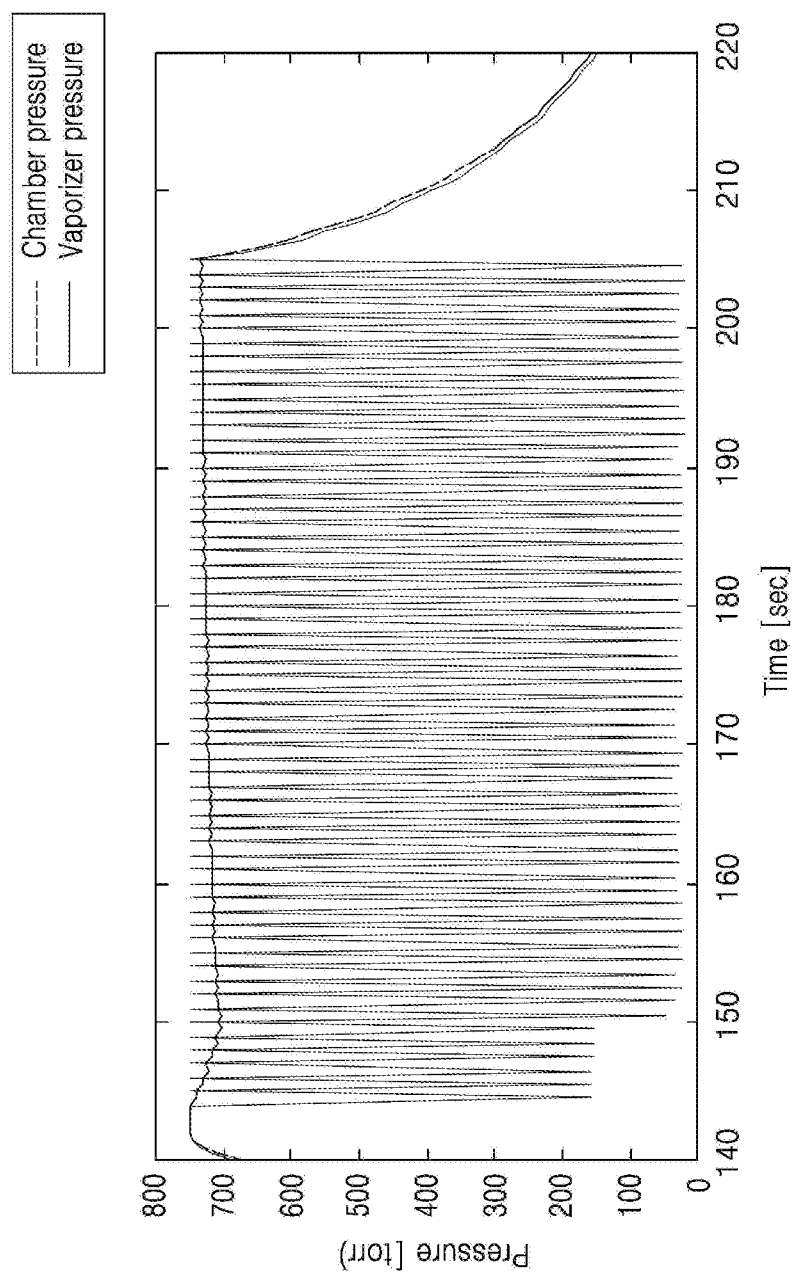
FIG. 20 is a view in which the inside of an impermeable sealed container is kept constant at pressure lower than atmospheric pressure to be forced to convection to raise the temperature, as an example according to the present invention.

In FIG. 20, pressure in a chamber is kept constant at about 700 torr, which is pressure lower than atmospheric pressure, from about 140 seconds to about 200 seconds. Internal pressure of a impermeable sealed container directly connected to a vaporizer repeatedly reaches the lowest and highest pressures several times as exhaust and intake are repeated, after which the pressure in the chamber and pressure in the vaporizer coincide and fall (since the vaporizer and the impermeable sealed container are directly connected to each other, the pressures in the vaporizer and the impermeable sealed container are the same).

Figure 21:
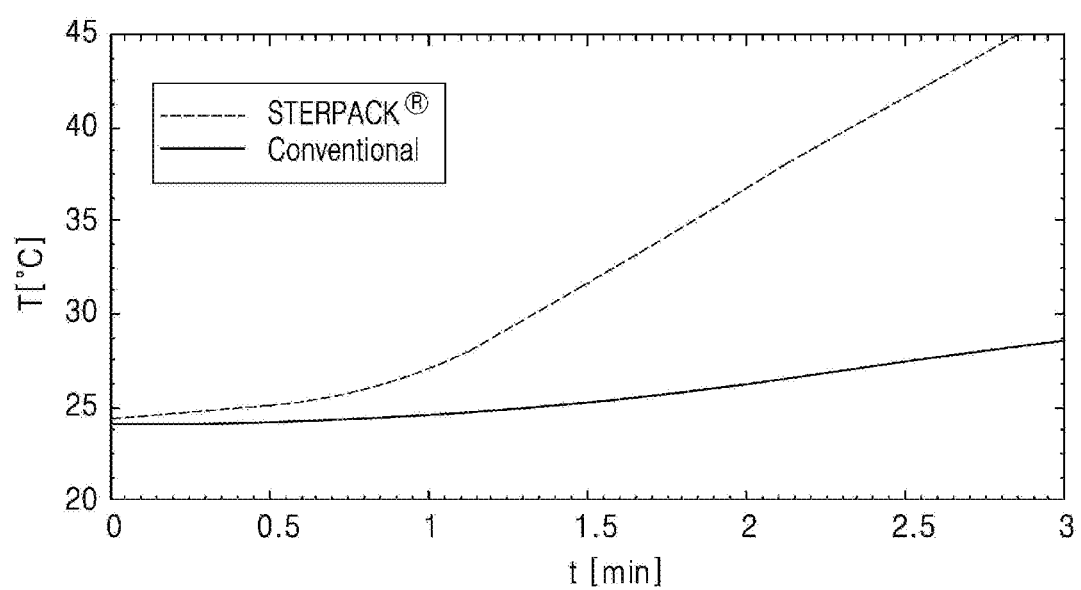
FIG. 21 is a view in which a graph of temperature rise of a general pouch and a graph of temperature rise of an impermeable sealed container applicable to a sterilizer of the inventor (applicant) are compared, as an example according to the present invention.

FIG. 21 is a view in which a graph of temperature rise of a general pouch (Tyvek) and a graph of temperature rise of an impermeable sealed container (STERPACK®) applicable to a sterilizer of the inventor (applicant) are compared, as an example according to the present invention. Typical pouches are only heated from 25° C. to 30° C. in 3 minutes with a temperature rise of 4° C. to 6° C. per minute. However, when an impermeable sealed container applicable to the present invention of the inventor is used, it can be seen that the temperature rises up to about 10° C. per minute and reaches 45° C. in less than 3 minutes.

Meanwhile, in drying and vacuuming to obtain moisture check and base pressure during the "SR process", when internal pressure of the impermeable sealed container reaches pressure lower than water vapor pressure through vacuum evacuation, the total amount of water is estimated by measuring the evaporation of water, and when reaches certain pressure, a channel is blocked to isolate the inside of the impermeable sealed container and then a change in pressure is measured.

For example, when the inside of the impermeable sealed container reaches pressure lower than the water vapor pressure through vacuum evacuation, water inside the impermeable sealed container begins to evaporate. When all channels are blocked in this state, the internal pressure of the impermeable sealed container is increased by the evaporated water. In addition, by measuring a rate of a change in the internal pressure of the impermeable sealed container per unit time, the amount of water in the impermeable sealed container may be estimated inversely, which is shown in more detail in FIGS. 22 and 12.

Figure 22:
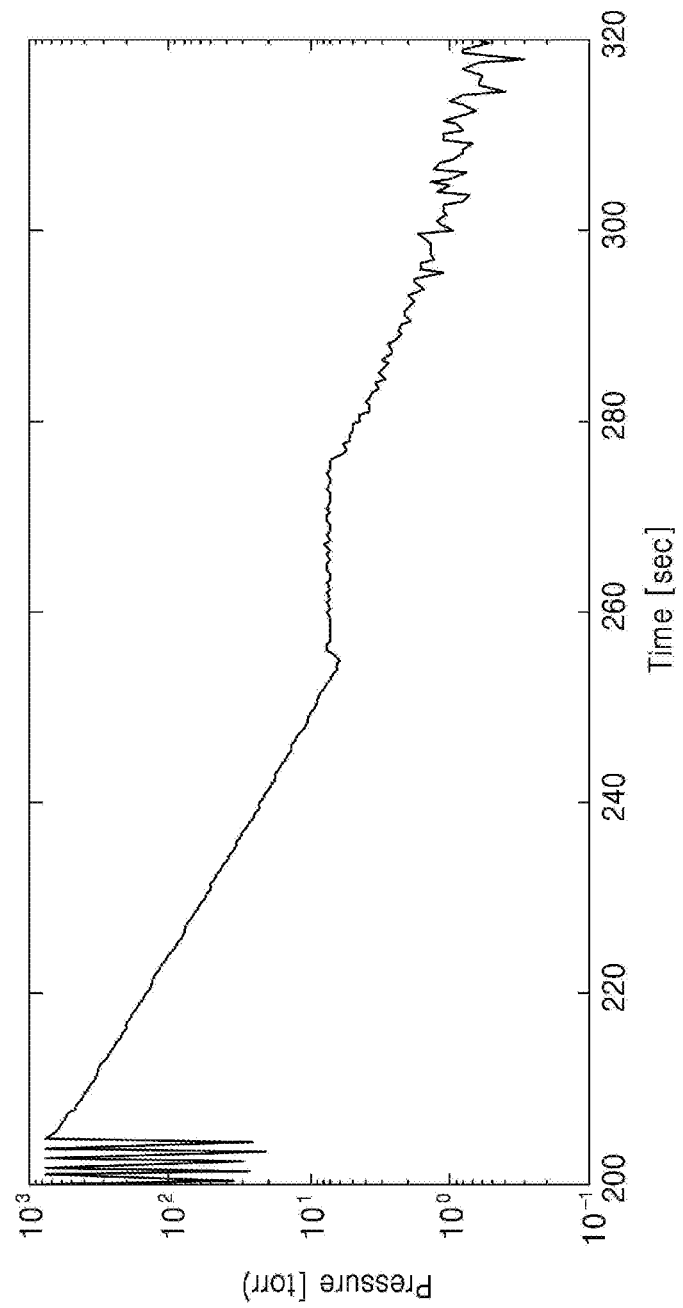
FIG. 22 is a view in which, when an impermeable sealed container reaches pressure lower than water vapor pressure through vacuum evacuation in moisture check, drying, and vacuuming, the total moisture is estimated by measuring the amount of water evaporated, and when the impermeable sealed container reaches certain pressure, a valve is closed to isolate the inside of the impermeable sealed container and a relationship between time and pressure is shown to measure a change in pressure, as an example according to the present invention.
Figure 23:
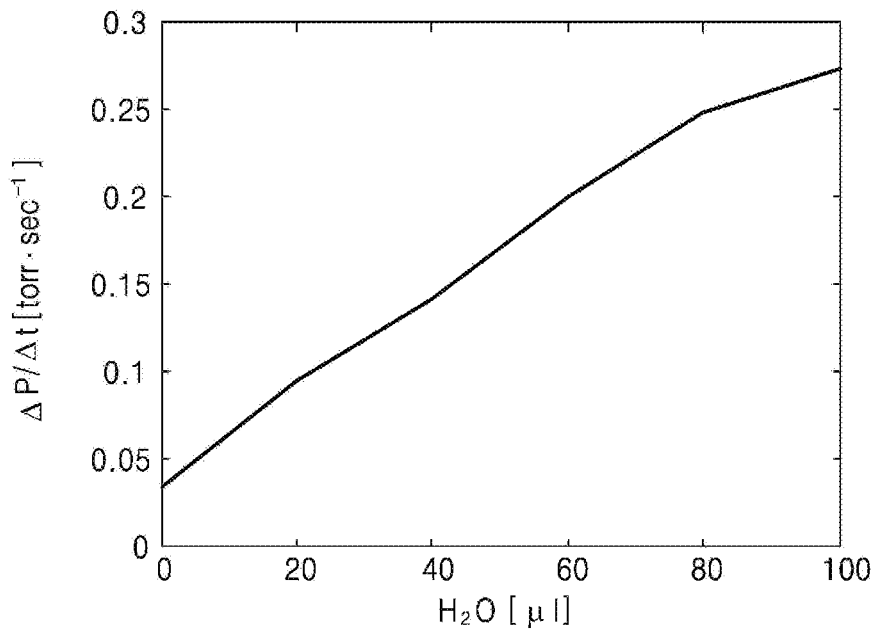
FIG. 23 is a view of a rate of a change in pressure per unit time in proportion to the amount of moisture in an impermeable sealed container, as an example according to the present invention.

In FIG. 22, after the internal pressure of the impermeable sealed container is lowered to 5 torr through vacuum exhaust, internal moisture starts to evaporate, and then the internal pressure is slightly increased. In FIG. 23, a rate of a change in pressure of a impermeable sealed container per unit time is proportional to the amount of water. The higher the amount of water in the impermeable sealed container, the greater the amount of water evaporated, and thus the rate of a change in pressure per unit time also increases.

Figure 24:
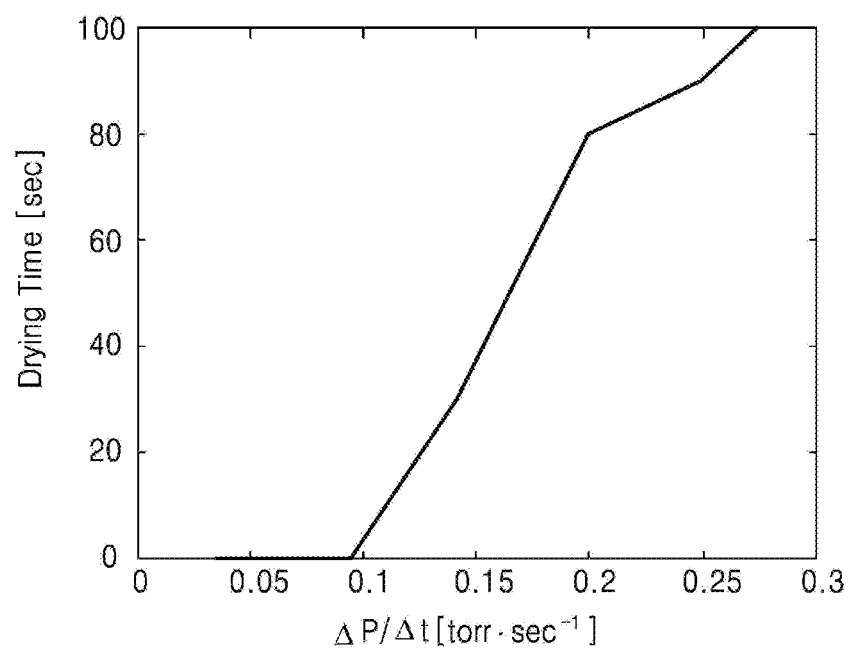
FIG. 24 is a view of a relationship between a measured rate of the change in pressure per unit time and drying time, as an example according to the present invention.

FIG. 24 shows a relationship between a measured rate of the change in pressure per unit time and a drying time, as an example according to the present invention. It can be seen that the drying time varies depending on the rate of the change in pressure per unit time for efficient drying (the overall trend is that the greater the rate of the change in pressure per unit time, the greater the drying time.).

For example, in 100 μl (=0.1 ml) of FIG. 23, a rate of a change in pressure per unit time is about 0.27 torr/sec. In the case of excessive moisture, a drying process may be stopped and an error may be generated (see FIG. 24).

Figure 25:
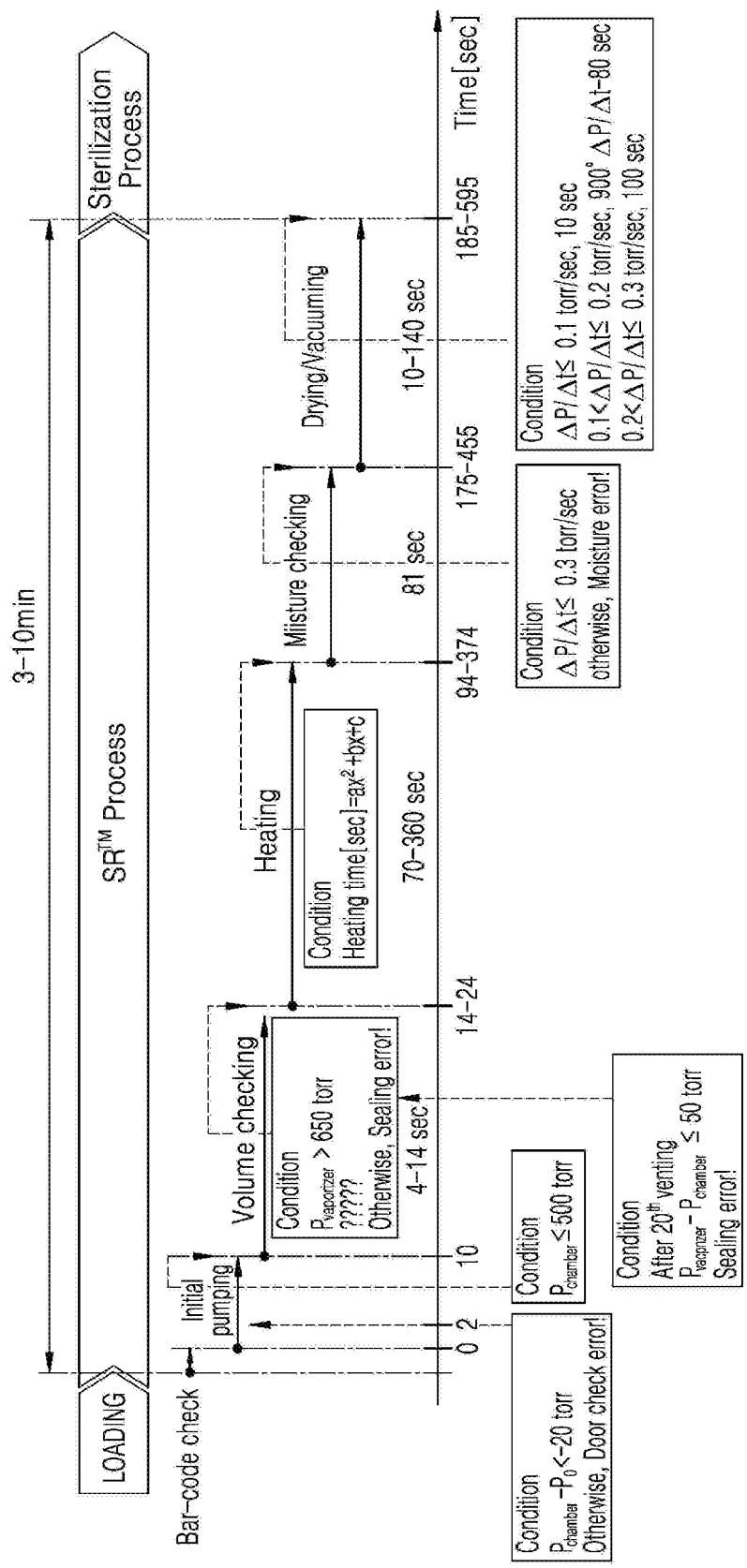
FIG. 25 is a schematic view of a heating and drying process (SR process) during sterilization, as an example according to the present invention.

FIG. 25 is a schematic view in time of a heating and drying process (SR process) during sterilization, as an example according to the present invention, wherein a time required for each step and specific numerical values described herein are only examples, and it is obvious to one of ordinary skill in the art that the time required for each step and the specific numerical values can be adjusted to obtain the effect of the present invention.

An embodiment according to the present invention is listed as follows, and the same as the means for solving the above problems.

According to an aspect of the present invention, a sterilizer includes an impermeable sealed container directly connected to a vaporizer.

Preferably, the impermeable sealed container is flexible and elastic, thereby freeing contraction and expansion of the volume according to external pressure.

Also preferably, the vaporizer is connected to a vacuum pump and an exhaust port to perform independent pressure control through a valve.

More preferably, the vacuum pump and the exhaust port are also connected to a chamber to enable independent pressure control through the valve.

Alternatively preferably, the vaporizer is directly connected to the impermeable sealed container to control pressure of the container by controlling pressure of the vaporizer.

Alternatively more preferably, the vacuum pump and the exhaust port are connected together to a plasma source.

Alternatively preferably, the impermeable sealed container is supplied with air and a sterilant through the vaporizer.

Even more preferably, the supply of air is made through the vaporizer to increase heating efficiency inside the impermeable sealed container.

Still more preferably, an effective volume of a sterilized article is checked by measuring the time that the air is supplied to the impermeable sealed container.

The accuracy of the effective volume check is increased by measuring the time at which internal pressure of the impermeable sealed container reaches a specific value.

In addition, in order to increase the accuracy of the volume check, the air is repeatedly injected with an air injection time and a holding time.

Preferably, the holding time allows the impermeable sealed container to expand sufficiently to increase the accuracy of the volume check.

Also preferably, time resolution is controlled by adjusting a ratio of the injection time and the holding time.

Alternatively preferably, a method of measuring the number of venting cycles as non-integer rational numbers is introduced using a median formula until the internal pressure of the impermeable sealed container reaches a specific value.

Meanwhile, when the effective volume check of the sterilized article is completed, the air supply is cut off and a change in pressure per unit time in the impermeable sealed container is measured to detect a pouch sealing error of the impermeable sealed container.

Meanwhile, the sterilizer measures the effective volume of the sterilized article, and thus a heating time is varied according to the value so that the temperature is efficiently raised.

According to another aspect of the present invention, a sterilization method includes (S1) initializing to identify a chamber, an impermeable sealed container containing a sterilized article, and a locking device; (S2) heating and drying the chamber and the impermeable sealed container; (S3) sterilization; and (S4) residue checking, venting, and user confirming.

(S2) The heating and drying of the chamber and the impermeable sealed container includes (P1) initial pumping to prepare a low level vacuum; (P2) checking an effective volume of the sterilized article; (P3) heating the impermeable sealed container and the chamber; (P4) checking residual moisture; and (P5) drying and vacuuming to obtain base pressure.

(P4) the moisture check includes: (R1) residue checking; (R2) purifying; (R3) venting; and (R4) user confirming.

In (P2) the volume check of the effective volume of the sterilized article, the effective volume is checked by measuring an internal pressure value of the impermeable sealed container and measuring a time to reach a specific value.

After (P1) the initial pumping of preparing a low level vacuum, the channel between the vaporizer and the chamber is opened to match the pressure value, and air is injected into the impermeable sealed container, but an injection time of the air and the time for blocking the injection and holding the blocking are separated and repeated to increase the accuracy of the effective volume check.

Also, time resolution is controlled by adjusting a ratio of the injection time to the holding time.

In addition, the accuracy of the effective volume check is increased by making the number of venting cycles as non-integer rational numbers using a median formula until the internal pressure value of the impermeable sealed container reaches a specific value.

In (P3) the heating the impermeable sealed container and the chamber, the inside of the chamber is kept constant at pressure lower than atmospheric pressure and heated through forced convection.

A time required for the heating varies depending on the effective volume of the sterilized article.

In (P4) the checking of residual moisture, when the inside of the sealed container reaches pressure lower than water vapor pressure through vacuum exhaust, the amount of water evaporated is measured to estimate the total amount of water.

In addition, when the inside of the sealed container reaches certain pressure through the vacuum exhaust, the valve is closed to isolate the inside of the impermeable sealed container, and then the change in pressure is measured.

Also, a rate of the change in pressure per unit time increases in proportion to the amount of moisture in the impermeable sealed container.

According to the measured rate of the change in pressure per unit time, in (P5) the drying and vacuuming of obtaining base pressure, the drying process time is variable.

After (P2) the checking of the effective volume of the sterilized article, in order to confirm a lamination error or damage of the impermeable sealed container, the valve is closed and the internal pressure of the impermeable sealed container is measured. After measuring a change in the internal pressure in time to detect the lamination error or damage, (P3) the heating of the impermeable sealed container and the chamber is performed.

Meanwhile, features of the technical configuration of the present invention are as follows.

A vaporizer is connected directly to an impermeable sealed container, and thus the vaporizer may directly supply a sterilant and may supply air. The impermeable sealed container containing a sterilized article is flexible and elastic, so the volume is free to contract and expand according to external pressure. The vaporizer may be connected to a vacuum pump and an exhaust port for independent pressure control through a valve.

In addition, the vacuum pump and the exhaust port are connected to a chamber to enable independent pressure control through the valve. The vaporizer may be directly connected to the impermeable sealed container to control pressure of the impermeable sealed container together with vaporizer pressure. The supply of air to the impermeable sealed container may be performed through the vaporizer to increase heating efficiency inside the impermeable sealed container.

The SR process has been described above, and the SC process will be described below.

[SC Process]

Meanwhile, the SC process includes residue check, purification, venting, and user confirming.

The residue check is to measure a residual sterilant and the purification is to form a vacuum such that the sterilant is removed by evaporation.

After removing the sterilant sufficiently by exposure to a vacuum, the vaporizer and the impermeable sealed container are separated and the impermeable sealed container is sealed such that external air does not flow in while the pressure inside the impermeable sealed container forms a vacuum. A chamber is then vented in the venting operation to open a sterilizer and a user takes out and stores the sealed impermeable sealed container (user confirming).

External air is not introduced into the impermeable sealed container completed until the purification operation. If external air enters, it can be polluted by foreign materials. Therefore, the venting in the SC process is different from the venting in the SR process described above.

The invention claimed is:

1. A sterilizer comprising:
   an impermeable sealed container directly connected to a vaporizer, flexible and elastic, and free of volume contraction and expansion under external pressure; and
   a processor configured to check an effective volume of a sterilized article by measuring a time for which air is supplied to the impermeable sealed container.

2. The sterilizer of claim 1, wherein the vaporizer is connected to a vacuum pump and an exhaust port to perform independent pressure control through a valve, and the vacuum pump and the exhaust port are also connected to a chamber to enable independent pressure control through the valve.

3. The sterilizer of claim 1, wherein the vaporizer is directly connected to the impermeable sealed container to control pressure of the impermeable sealed container by controlling pressure of the vaporizer, and the impermeable sealed container is supplied with air and a sterilant through the vaporizer.

4. The sterilizer of claim 1, wherein the impermeable sealed container is supplied with air and a sterilant through the vaporizer, and the supply of air is made through the vaporizer to increase heating efficiency inside the impermeable sealed container.

5. The sterilizer of claim 1, wherein accuracy of the effective volume is increased by measuring a time at which internal pressure of the impermeable sealed container reaches a specific value.

6. The sterilizer of claim 1, wherein, in order to increase accuracy of the effective volume, air is repeatedly injected with an air injection time and a holding time.

7. The sterilizer of claim 6, wherein time resolution is controlled by adjusting a ratio of the injection time and the holding time.

8. The sterilizer of claim 1, wherein introduced is a method of measuring a number of venting cycles until internal pressure of the impermeable sealed container reaches a specific value, as non-integer rational numbers, using a median formula.

9. The sterilizer of claim 1, wherein, when the effective volume check of the sterilized article is completed, supply of the air is cut off and a change in pressure per unit time in the impermeable sealed container is measured to detect a pouch sealing error of the impermeable sealed container.

10. A sterilization method comprising:
    initializing to identify a chamber, an impermeable sealed container containing a sterilized article, and a locking device;
    heating and drying the chamber and the impermeable sealed container;
    sterilizing; and
    residue checking and completing a process.

11. The sterilization method of claim 10, wherein the heating and drying of the chamber and the impermeable sealed container comprises:
    initial pumping to prepare a low level vacuum;
    checking an effective volume of the sterilized article;
    heating the impermeable sealed container and the chamber;
    checking residual moisture; and
    drying and vacuuming to obtain base pressure.

12. The sterilization method of claim 11, wherein, in the checking of the effective volume of the sterilized article, the effective volume of the sterilized article is checked by measuring an internal pressure value of the impermeable sealed container and measuring a time to reach a specific value.

13. The sterilization method of claim 12, wherein, in the initial pumping of preparing the low level vacuum, pressure of the chamber is relatively low compared to pressure of the impermeable sealed container, and thus a channel for forming a vacuum of the sealed container is ensured.

14. The sterilization method of claim 12, wherein, after the initial pumping of preparing the low level vacuum, a channel between a vaporizer and the chamber is opened to match a pressure value, air is injected into the impermeable sealed container, and an injection time of the air and a holding time for blocking injection of the air and holding the blocking are separated and repeated to increase accuracy of the effective volume check.

15. The sterilization method of claim 11, wherein, in the heating of the impermeable sealed container and the chamber, the inside of the chamber is kept constant at pressure lower than atmospheric pressure to facilitate the injection of air into the impermeable sealed container.

16. The sterilization method of claim 15, wherein a time required for the heating varies depending on the effective volume of the sterilized article.

17. The sterilization method of claim 11, wherein, in the checking of residual moisture, when the inside of the impermeable sealed container reaches pressure lower than water vapor pressure through vacuum exhaust, an amount of water evaporated is measured to estimate a total amount of water.

18. The sterilization method of claim 17, wherein, when the inside of the sealed container reaches certain pressure through the vacuum exhaust, a valve is closed to isolate the inside of the impermeable sealed container, and then a change in pressure is measured.

19. The sterilization method of claim 18, wherein, according to the measured rate of the change in pressure per unit time, in the drying and vacuuming to obtain base pressure, a drying process time is variable.

* * * * *